United States Patent
Wuttke et al.

(10) Patent No.: US 11,774,456 B2
(45) Date of Patent: Oct. 3, 2023

(54) METHOD TO ANALYZE COMPOUNDS IN BIOLOGICAL SAMPLES

(71) Applicant: magtivio b.v, Nuth (NL)

(72) Inventors: Mario Wuttke, Gangelt (DE); Viorel Rusu, Eygelshoven (NL); Erik Ruijters, Maastricht (NL); Gerbert Schaap, Heerlen (NL); Sven Goethel, Troisdorf (DE)

(73) Assignee: magtivio b.v, Heerlen (NL)

( * ) Notice: Subject to any disclaimer, the term of this patent is extended or adjusted under 35 U.S.C. 154(b) by 7 days.

(21) Appl. No.: 17/696,976

(22) Filed: Mar. 17, 2022

(65) Prior Publication Data

US 2022/0206010 A1 Jun. 30, 2022

Related U.S. Application Data

(60) Division of application No. 16/427,907, filed on May 31, 2019, now Pat. No. 11,307,207, which is a continuation of application No. PCT/EP2017/081270, filed on Dec. 1, 2017.

(30) Foreign Application Priority Data

Dec. 2, 2016 (WO) ................ PCT/EP2016/079668

(51) Int. Cl.
| | | |
|---|---|---|
| *G01N 33/68* | (2006.01) | |
| *B01L 3/00* | (2006.01) | |
| *G01N 21/64* | (2006.01) | |
| *G01N 33/483* | (2006.01) | |

(52) U.S. Cl.
CPC .... *G01N 33/6848* (2013.01); *B01L 3/502715* (2013.01); *B01L 3/502753* (2013.01); *G01N 21/64* (2013.01); *G01N 33/4833* (2013.01); *B01L 2300/069* (2013.01); *B01L 2300/12* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,111,807 | A | 9/1978 | Boomus et al. |
| 8,524,794 | B2 | 9/2013 | Muller et al. |
| 2001/0008931 | A1 | 7/2001 | Van Antwerp et al. |
| 2008/0097241 | A1 | 4/2008 | Maltezos |
| 2013/0017545 | A1 | 1/2013 | Yong et al. |

FOREIGN PATENT DOCUMENTS

| | | |
|---|---|---|
| WO | 2008111013 A2 | 9/2008 |
| WO | 2014022133 A1 | 2/2014 |

OTHER PUBLICATIONS

"MagnaMedics: ""MagSIMUS products for biological sample preparation""", Jan. 1, 2015 (Jan. 1, 2015), MagnaMedics BV, Geleen, The Netherlands, XP002756273,".
J. Colloid Interface Sci 1968, pp. 26, 62-69.
Langmuir 2005, pp. 21, 10763-10769.
J. Colloid Interface Sci 2005, pp. 283, 392-396.
Non-Final Office Action dated Apr. 16, 2021 for U.S. Appl. No. 16/427,907.
Final Office Action dated Jul. 22, 2021 for U.S. Appl. No. 16/427,907.
Notice of Allowance dated Dec. 16, 2021 for U.S. Appl. No. 16/427,907.
Uwugiaren, N. Optimization of Analytical Procedure for Protein Analysis in Fresh Frozen Laser Microdissectioned Human Tissue, Bachelor Thesis Scheikunde, Universiteit Van Amsterdam, Jul. 2016 (Year: 2016).
Porvair Filter Group, Industrial Process, retrieved from internet file:///C:/Users/xxu/Documents/e-Red%20Folder/16427907/World%20class%20filtration%20solution%202009.pdf (Year: 2009).

*Primary Examiner* — Xiaoyun R Xu
(74) *Attorney, Agent, or Firm* — Eschweiler & Potashnik, LLC

(57) ABSTRACT

Various embodiments of the present disclosure relate to a method for analyzing target compounds from a fluid or dried biological sample by using a microfluidic sample device including a hollow cartridge and an absorbent body unit.

8 Claims, No Drawings

METHOD TO ANALYZE COMPOUNDS IN BIOLOGICAL SAMPLES

REFERENCE TO RELATED APPLICATION

This Application is a Divisional of U.S. application Ser. No. 16/427,907, filed on May 31, 2019, which is a continuation of International Application number PCT/EP2017/081270, filed on Dec. 1, 2017, which claims priority to International Application number PCT/EP2016/079668, filed on Dec. 2, 2016. The contents of the above-referenced Patent Applications are hereby incorporated by reference in their entirety.

BACKGROUND

There are a number of approaches to analyze a biological sample. For example, a biological sample may be analyzed by immunoassay, mass spectrometry (e.g., LC-MS, LC-MS/MS), or the like. While these approaches may be able to achieve accurate measurements of the biological sample, there are many substances (e.g., proteins, phospholipids, etc.) in the biological sample that may have negative effects on these measurements. Thus, biological samples are typically prepared before measurement to minimize the negative effects of these substances.

DETAILED DESCRIPTION

In the pre-analytic preparation for liquid biological materials like blood, serum, saliva, urine or plasma, the clinically relevant liquids are typically investigated through immunoassays, particularly ELISA assays on the quantitative content. To diagnose diseases, low molecular weight organic compounds need to be determined at low levels. Low molecular weight organic compounds, like trace components, that need to be analyzed, may be naturally occurring in samples as compounds (e.g. vitamins or metabolites), but may also be occurring in a sample by an exogenously addition such as medicines or drugs.

In recent years, the LC-MS (or LC-MS/MS) turns as an alternative to immunoassays. Typically to accomplish such an analytical approach, the representative sample is separated out of complex liquid biological materials by precipitation and subsequent centrifugation of abundant proteins and a subsequently separation of low molecular weight components enriched within the sample using a reversed phase LC and become identified and quantified by mass spectrometry (MS) and/or UV-VIS.

Although very sensitive measurement and precise results can be achieved with a possible mass spectrometry readout, there are many substances from the biological sample source that have a negative effect on such measurements. These substances form a so called sample matrix and they are composed of abundant proteins, phospholipids, lipids, and salts in whole blood, serum, plasma etc. They are also present in plant extracts or food products and cause matrix effects.

It is known that depending on the type of sample and the study goal, the qualitative and quantitative content of a target compound can be measured on different instrumental platforms and for different end-uses such as clinical checks, doping tests, forensic-toxicological tests or food checks. The samples have to be representative and prepared before the measurement to minimize matrix effects that can reduce sensitivity and accuracy.

The analytical process from sampling to the end result is basically divided into six steps:
1. Sample reconstitution for dried samples
2. Sample extraction
3. Sample preparation
4. Sample fractionation
5. Sample detection
6. Sample data control Biological samples are multi-component systems with a very complex composition, which often contain fatty acids, proteins, salts, lipids, acids, bases, and organic components as constituents. Some of these components interfere with the analysis since these components have similar characteristics as the substances to be analyzed.

In the state of the art analysis, the analytical target parameters which are usually substances to be analyzed, like trace components, are present in low concentration in the samples which are difficult to isolate and to measure. Therefore, depending on the origin of samples and type of components of interest, the task of the present invention is to improve the handling for a preparation of fluid and dried biological samples by reducing the work-flow, remove interfering abundant compounds of the samples in order to isolate specific compounds and/or to enrich these in the remaining sample within a predefined volume as a part of the sample preparation step.

Herein the invention discloses a method for sample preparation with a positive selection of compounds and substances for example trace components and a negative selection of abundant compounds of a sample using specific solvent systems and magnetic beads for the sample preparation as a pre-analytical step.

The invention discloses a sample preparation method and the use for such applications, including the following features that an aqueous solution of a reconstitution buffer composition comprising acids, bases and/or salts besides other components is added to the sample like fluid or dried biological samples and the sample compounds become separated from the fluid or reconstituted biological sample whereby the analytic compounds like trace compounds may remain in the aqueous solution of the reconstitution buffer composition.

The method is generally focused on the subject to analyze target analytic compounds from a fluid or dried biological sample by using a microfluidic sample device comprising of a hollow cartridge and an absorbent body unit, a) wherein the adsorbent body unit is prepared with a coating of artificial antioxidants as active ingredients of the coating,
b) wherein the adsorbent body unit is positioned at the distal end of the hollow cartridge and the proximal end of the hollow cartridge comprises a passage that can be connected to a pipette and/or a pipette head of an automated operation device,
c) wherein at least one reconstitution buffer composition is dispensed in a vial or well,
d) reconstitution of the dried biological sample using the reconstitution buffer composition,
e) the fluid or reconstituted dried biological sample is soaked and stored in the absorbent body unit,
f) the fluid or reconstituted dried biological sample is aspired into the hollow cartridge through the absorbent body unit using a predefined amount of the reconstitution buffer composition wherein the proximal end of the hollow cartridge comprises a passage that is connected to a pipette tip and/or an operation device able to change its positions in sequential steps, g) the fluid or reconstituted dried biological sample becomes stored in the hollow cartridge temporarily,
h) the fluid or reconstituted dried biological sample is released back into the vial or well and then aspirated back again into the hollow cartridge at least one time in order to achieve a higher concentration of the sample compounds of the reconstituted dried biological sample,
i) wherein a predefined volume of the fluid or reconstituted dried biological sample is transferred into a new well or vial,
j) wherein a removal of abundant non-analytical compounds is achieved by adding an internal standard, coated magnetic beads and a depletion buffer to the fluid or reconstituted dried biological sample,
k) separating the abundant compounds of the fluid or reconstituted or re-solubilized biological sample by using a magnetic separator,
l) receiving the target analytical compounds of the fluid or reconstituted dried biological sample in the supernatant, and/or
m) binding at least some of the received compounds to another type of coated magnetic beads and elute these compounds thereafter,
o) analyze the received compounds by various readouts, wherein step c) is related to, in some embodiments, dried biological samples soley.

The separation of abundant compounds like proteins from the fluid or reconstituted dried biological sample may include the step of adding a reconstitution buffer composition, a first magnetic, mobile solid phase support like magnetic beads preferably coated magnetic silica beads e.g. magnetic silica gel particles to the sample and adding a depletion buffer comprising polar, organic solvents with an aqueous solution of acids, bases and/or salts, leading to an adsorption of the abundant compounds like e.g. proteins to the magnetic beads or other magnetic mobile solid support particles and a separation of the magnetic beads or magnetic particles with the adsorbed abundant compounds by magnetic force with a magnetic separator like a magnet, wherein the analytic compounds like trace components remain in the liquid phase and/or a second magnetic mobile solid phase support is added to the remaining liquid phase in order to adsorb remaining abundant compounds or to absorb the analytic compounds like trace compounds to the surface of the magnetic beads or magnetic particles and elute these trace or abundant compounds thereafter for analysis.

Magnetic beads in the present invention may include silica beads or particles with one or more magnetic cores as in a preferred embodiment of the invention but not limited to it. Therefore it is also possible to use other magnetic bead types or particles like activated carbon, fullerenes, latex, polyvinyl alcohol, melamine, chitin etc. with one or more magnetic cores as long as a sufficient binding of the abundant interfering or analytical compounds can be achieved.

The present invention relates to a method for isolating compounds from a biological sample like trace compounds from fluid or dried biological samples, wherein the samples comprises different kind of samples like whole blood, plasma, serum, urine, cerebrospinal fluid, cerumen, nasal secretions, saliva, tears, breast milk, gastric juice, bronchoalveolar fluid, nipple aspirate fluid, amniotic fluid, bile, cervico-vaginal fluid, seminal plasma fluid food and/or feed samples. The sample preparation can be carried out in a kit-based format. In particular, the present invention enables selective isolation of compounds like trace components in the presence of matrix effect-causing compounds. Compounds to be isolated can be trace components for example, vitamins, especially vitamin C and vitamin B1 to vitamin B12, immunosuppressants, mycotoxins, etc. by the use of a controlled depletion of abundant compounds in the presence of a solid phase support like silica gel particles, in particular in the presence of silica particles with magnetic cores.

The invention relates to the field of readouts for sample preparation for UHPLC, HPLC, LC/MS, LC/MS/MS, LC/UV-VIS, capillary LC, capillary electrophoresis, immunoassays, including ELISA and other tests that of the sample preparation method for the detection trace components and/or low molecular weight compounds for analysis in complex clinical and non-clinical samples are aligned. Clinical samples for the purposes of the invention include homogenized tissue, whole blood, dried blood, tissue culture, plasma, serum, urine, saliva, tears, spinal fluid, tissue fluid, amniotic fluid, follicular fluid and hemolyzed blood. Non-clinical samples are directed to food, beverages, water samples, environmental samples and liquid fermentation media.

As a proper diagnosis of diseases is required for an appropriate therapy, a rapid diagnosis has to take place in order to enable a reliable clinical decision. Thus, the invention provides not only the possibility of preparing a biological sample for analysis but also a method to determine and monitor sample substances like trace components getting isolated.

An analytical sample preparation process of a biological sample is aiming to transform the original sample in a state to enable the analyze of the trace components of interest. This has to be done in a sample preparation step in order to avoid any disturbing matrix effects or matrix influences during the downstream analytical process. This pre-analytical sample preparation step has to be done for all kind of biological samples, for dried samples as well as for fluid samples. As biological samples comprise the analytical targets like trace components in a fluid state the preparation step can start without reconstituting or re-solubilizing the biological sample.

A dried biological sample for analytical detection has to be transformed or reconstituted in a fluid state without the sample being contaminated, losing the whole or parts of the sample content and that the preparation and analysis can be done easily by an operation device process. The transformation or reconstitution has to be conducted before the analytical process starts.

In the underlying invention the fluid or reconstituted dried biological samples are stored and released from at least one microfluidic sampling device comprising a cartridge and an absorbent body unit. The cartridge encompasses a tubular form at least a partly hollow cylindrical shape which enables the cartridge getting attached to an operation device like a pipette or an automated operation device like a pipette head of a working platform with a tubular shift wherein the operation device or automated operation device is able to change its positions in sequential steps. The tubular form of the cartridge enables a fluid flushing. E.g. Eppendorf pipettes are compatible/attachable to the operation device or automated operation device. The cartridge can encompass a membrane, but can also be membrane-free.

A fluid or reconstituted dried biological sample is adherent to a certain absorbent body unit like a filter paper, a pipette tip or porous material with a defined liquid sample volume uptake. The absorbent body unit uptake is in the range between 5 and 100 µl and preferably between 15 and 75 µl. It can be fine tuned using an adsorption coefficient of the e.g. modified sintered porous material used as adsorbent body of cartridge with specific hydrogel coatings.

Concerning the pre-defined volumes for the reconstitution of the fluid or dried samples a pre-defined volume between 3× and 20× adsorption volume of the absorbent body unit can be used, most preferred between 3× and 10×. The greater the reconstitution buffer volume used the greater the dilution factor is introduced. At the end of the process the reconstitution sample volume has to be subtracted from the dead volume of the adsorbent body that also accommodates a reconstituted sample that will stay in it.

When low pre-defined reconstitution buffer composition (e.g. 3×) are used and the dilution factors introduced are smaller but also in a adsorbent unit it will be kept due to the dead volume more concentrated of the reconstituted sample. Therefore the exact pre-define volumes for the fluid or dried samples are application driven.

To identify and evaluate the proper materials of the absorbent body unit an activation and chemical coating to these adsorbent body units are necessary to enable the biological fluid (e.g. whole blood) or reconstituted dried sample uptake and the preservation of the sample to get a specific biological fluid uptake and release again. In order to protect specific target compounds (e.g. vitamins like A, E, B, D, F, but not limited to these compounds) from susceptible oxidation, when stored in dried form within the absorbent body, an adding of artificial antioxidants as an active ingredient of the coating of the adsorbent body unit is prepared. The coating of the adsorbent unit is comprising compositions selected from a group of compounds like Butylated Hydroxyanisole (BHA), Butylated Hydroxytoluene (BHT), -ethoxyquin, polyvinylpyrrolidone (PVP), polyacrylic acid (PAA), polyethyleneimine (PEI), sorbitan esters, polyethoxy sorbitan esters octylphenoxypolyethoxyethanol, $Na_2$-EDTA, Na-citrate, hydrogels or mixtures of thereof. The concentration range of these coating compounds is given in a range between 20 and 200 ppm. This concentration range refers just to the antioxidant list of compounds added such as BHA, BHT and ethoxyquin.

As commercially available sintered polymeric filters used as adsorbent body units are very hydrophobic, hence the hydrophilic biological liquids to be accommodated, stored and thereafter analyzed do not wet these kinds of materials thus it is not possible to accommodate and store them within such materials. Therefore the inner and outer surface of such materials has to be modified and reverted from highly hydrophobic to more hydrophilic keeping also some hydrophobic spots randomly distributed among the predominant hydrophilic surface of the adsorbent body unit in order to increase the ability of water or aqueous biological samples to wet the surface of such materials. Additionally the modification of the adsorbent body is availed to suppress oxidation of various compounds to stabilize the sample. This is done by a coating of the adsorbent unit comprising compositions selected from a group of compounds like Butylated Hydroxyanisole (BHA), Butylated Hydroxytoluene (BHT), -ethoxyquin, polyvinylpyrrolidone (PVP), polyacrylic acid (PAA), polyethyleneimine (PEI), sorbitan esters, polyethoxy sorbitan esters octylphenoxypolyethoxyethanol, $Na_2$-EDTA, Na-citrate, hydrogels or mixtures of thereof.

To achieve such surface modification the adsorbent units which are based on sintered polymeric materials these adsorbent units are treated with hydrophilic/hydrophobic block materials achieving stable coating with a proper orientation of functional groups such that the polar groups are oriented away from the surface with the result of increasing the water-wetting material properties. Hence the modification step of the surface is conducted by performing first pre-wash steps with bicarbonate buffer (pH 8.5) and acetate buffer (pH 5.5) by soaking the body filters in these buffers followed by subsequent rinsing with DD water and then by a coating and filling the adsorbent body materials with various hydrogel matrices e.g. various polymeric matrices like Butylated Hydroxyanisole (BHA), Butylated Hydroxytoluene (BHT), -ethoxyquin, polyvinylpyrrolidone (PVP), polyacrylic acid (PAA), polyethyleneimine (e.g. PEI), sorbitan esters (e.g Span 80), octylphenoxypolyethoxyethanol (e.g. Igepal, $Na_2$EDTA and Na citrate).

The adsorbent body unit prepared according to the previous embodiment of this invention enables an admission/uptake of a biological fluid sample and then upon drying for at least 1 h at room temperature and enables a long term sample storage at room temperature whereby the admission is caused by the capillary effect of the adsorbent body unit, which can be a filter paper, a capillary hydrophobic pipette tip or a porous sintered filter material. If a dried biological sample has to be analyzed, the dried biological sample has to be first reconstituted or re-solubilized by a reconstitution buffer composition in a small centrifuge tube or vial or a well of a microplate well. As a result the dried biological sample is transformed to a fluid sample which enables to perform the analytical readout process.

To reconstitute the fluid sample out of the dried biological sample the dried biological sample is soaked in the reconstitution buffer compositions by aspiring the reconstitution buffer through the absorbent body unit and then stored in the absorbent body unit as an incubation period of minimum 1 min. Afterwards the reconstituted dried biological sample is aspired into the hollow cartridge through the absorbent body unit using a predefined amount of the reconstitution buffer wherein the proximal end of the hollow cartridge comprises a passage that is connected to an operation device like a pipette and/or an automated operation device like a Hamilton working platform with a pipette head able to change its positions in sequential steps. The reconstituted biological sample becomes stored in the hollow cartridge temporarily and the fluid or reconstituted dried biological sample is released back into the vial or well and then aspired back again into the hollow cartridge at least one time in order to achieve a higher concentration of the sample compounds of the reconstituted dried biological sample. Then a predefined volume of the fluid or reconstituted dried biological sample is transferred into a new well or vial for the downstream analytical readout.

Additionally or alternatively the pre-analytical preparation process the step for the fluid or reconstituted dried biological sample by adding a reconstitution buffer composition for 1 to 600 sec to the sample and a multiple flushing in bidirectional or multi-directional way. The time and flushing mode influence the consistence of the reconstituted biological sample and implicitly the concentration of the target analytical compounds to be analyzed.

In order to further concentrate the trace compounds and/or analytical compounds from the dried biological samples it might be necessary to provide two or multiple microfluidic sample devices with the fluid and/or reconstituted dried biological sample. This means that at least one fluid and/or reconstituted sample is used as a reconstitution buffer for at least one other dried biological sample. Such a concentrated reconstituted sample can be used for the determination of trace analytical compounds at low concentration levels which are normally below the detection limit of the readout system.

It has to be mentioned that the reconstitution step for dried biological samples as well as the analytical preparation step for fluid samples can be done by an automation process like the use of several microfluidic sample devices on automated operating platforms with the result of process parallelization the use of several pipette head simultaneously. The samples through-put is depended on the connected type of the automated operating platform its capacity and/or design.

After releasing the reconstituted dried biological sample like mentioned in the previous embodiments in the foregoing paragraphs of the preparation the process is followed by the depletion of abundant compounds of the samples in order to minimize analytical detection issues induced by the presence in the sample of the highly abundant compounds. It was surprisingly found that the matrix compounds from the biological sample can easily and quickly get depleted and/or disconnected without significant changes within the compositions of the target trace analytical compounds in the sample. Additionally, some analytical trace compounds can be concentrated in a final clean-up step by a positive selection if needed.

It has to be mentioned that the percentage of trace compounds within the liquid biological materials as referred to the total amount is generally less than 10 wt.-%. In the present invention, the trace compound is ranging from 10exp-12 to 10exp-5 wt.-% preferably. In particular, the trace compound is in the range between 10 exp-9 to 10 exp-2 wt.-%.

Substances e.g. trace compounds which can be depleted and/or separated within the scope of the present invention can be vitamins, antibiotics, biomarkers of oxidative stress, amino acids and thiols, biomarkers of exposure, nitrogen compounds for protein adulteration. Especially mentioned and related to the above mentioned substances but not limited to the following list are substances like vitamin D and metabolites such as vitamin D2, D3, 3-epi-25-hydroxyvitamin D2, 3-epi-25-hydroxyvitamin D3, 1-alpha-25-dihydroxyvitamin D2, 1-alpha-25-dihydroxyvitamin D3, 25-hydroxyvitamin D2, 25-hydroxyvitamin D3, 1-alpha-hydroxyvitamin D3, 1, 25-dihydroxyvitamin D2, D3, thiamine: vitamin B1, thiamindiphosphate riboflavin: vitamin B2, niacin, nicotinamide, nicotinic Acid: vitamin B3, pyridoxine, pyridoxal, pyridoxamine: vitamin B6, folate: folic acid, folacin, pyridoxal-5'-phosphate cobalamin: vitamin B12, methylmalonic acid, biotin, pantothenic acid, ascorbic acid, ascorbate: vitamin C, ceftazidime, meropenem, ceftriaxone, ampicillin, cefazolin, ertapenem, cephalothin, benzylpenicillin, flucloxacillin, dicloxacillin, piperacillin, ticarcillin, malondialdehyde, 8-hydroxy-2-deoxyguanosine (8-OHdG), glutathione (GSH) glutathione disulfide, uric acid, isoprostanes, cysteinylglycine, homocysteine, 3-nitrotyrosine, cirulline, L-N-monomethyl-arginine, dimethyl-arginine, lysine, ornithine, histidine, arginine, triptophan, tyrosine, phenylalanine, valine, cystine, methionine, taurine, aspartic acid, serine, threonine, glutamic acid, alanine, glycine, nicotine, cotinine, nicotine-glucuronide, cotinine-glucuronide, 3-hydroxy-cotinine-glucuronide, nornicotine, nicotine-N-oxide, cotinine-N-oxide, 4-hydroxy-(3-pyridyl) butanoic acid, N-acetyl-S-(2-carbamoylethyl)-1-cysteine, N-acetyl-S—(N-methylcarbamoyl)-cysteine, cyanoethyl-mercapturic acid, 2-carboxy-1-methylethyl-mercapturic acid, dihydroxybutyl-mercapturic acid, N—(R,S)-acetyl-S-(2-carbamoyl-2-hydroxyethyl)-1-cysteine, 2-hydroxy-ethyl-mercapturic acid,3-hydroxy-1-methylpropyl-mercapturic acid, 2-hydroxypropyl-mercapturic acid, methyl-mercapturic acid, 2-hydroxy-1-phenylethyl mercapturic acid, 2-hydroxy-2-phenylethyl mercapturic acid, S-phenyl-mercapturic acid, S-benzyl-mercapturic acid, 3-OH-benzo[a]pyrene, 2-OH-fluorene, 1-OH-naphthalene, 1-OH-naphthalene, 2-OH-naphthalene, 3-OH-phenanthrene, 4-OH-phenanthrene, 9-OH-phenanthrene, 1-OH-pyrene, N-nitroso-anabasine, N-nitroso-nornicotine, 4-(methylnitrosamino)-1-(3-pyridyl)-1-butanol, 4-(methylnitrosamino)-1-(3-pyridyl)-1-butanol-glucuronide, 3-methyladenine, 3-ethyl-adenine, 1-N-etheno-adenine, 3-N-etheno-cytosine, 8-hydroxy-2-deoxy-guanosine, 2-methylthiazolidine-4-carbonyl-glycine, 2-methylthiazolidine-4-carboxylic acid, thiazolidine-4-carbonyl-glycine, thiazolidine-4-carboxylic acid, epirubicin, doxorubicin, paclitaxel, melamine, cyanuric acid, dicyandiamide, ammelide, ammeline can be separated and analyzed.

Matrix substances or compounds present in the samples like sugars, lipids, phospholipids and inorganic salts can be separated and analyzed with the method of the invention as well. By using the inventive method a tissue sample (biopsy), dried blood spots or body fluid (blood, plasma) can be taken from a person/animal and the diagnosis can be conducted outside the human or animal body. As a result the determination of the relevant diagnostic target substances like trace compounds according to the invention present a high significance and impact for monitoring existing quantities or their increase/decrease when followed over a time period.

Depletion of compounds means a partial reduction or a complete removal of high-molecular abundant compounds from a biological sample. This can be achieved through bonding, such as adsorption to a mobile magnetic solid phase support which, for example, consists of coated magnetic beads like silica, preferably mesoporous magnetic silica beads and a following separation with a magnetic separator like a magnet. The depletion can also be achieved with a solid support coating including matrix materials like e.g. polystyrene, melamine, polymethacrylate, polyamide, polyvinyl chloride, polyethylene, polypropylene, polyester, polycarbonate, polyacrylamide, agarose, chitin, dextran and polyvinyl alcohol.

In order to generate an easier depletion of the abundant proteins it is considered that the absorbent unit or the adsorbent body is comprising a configuration with a monoblock structure encompassing one layer or encompassing a multi block structure encompassing a multilayer structure wherein different functional groups densities of COOH, $NH_2$, OH, $TiO_2$, $ZrO_2$ in each single layer are comprised as a binding tool for a pre-cleaning step. In this way a pre-cleaning step can be initiated and accomplished as salts, phospolipids and the highly charged proteins can be already physically immobilized in the absorbent body leading to simplified sample matrix or residue after the sample reconstitution for detection the trace compounds to be measured.

The separation according to the invention is achieved by binding of abundant compounds to the coated magnetic particles that means to a magnetic mobile solid phase support whereas the trace components are left in the liquid phase. The magnetic mobile solid phase support can have different configurations in respect to dimensions, density, surfaces and core components. The configuration of the magnetic mobile solid phase support depends on the type, size and amount of the components and can differ in the configuration additionally if components should be bound to solid phase support as well.

Further purification of biological samples involves the isolation of the analytical compounds or components like trace components, which can be done by selective and reversible binding to the magnetic mobile solid phase support, for example in the form of magnetic silica particles, which may have a surface-modified structure. For example silica particles can be used as a first and second magnetic mobile solid phase support. The isolation of compounds like trace compounds can be performed by magnetic force after adsorption and after performing the separation or depletion of the matrix components of the liquid sample with the first mobile solid phase support. A further purification of the trace components can be achieved on magnetic silica particles single or multiple types in respect to their surface coating features having a specific function in achieving the selective binding of the trace compounds of interest onto the second mobile solid phase support by ionic, hydrophobic, π-π interactions, as well as metal-coordination interactions. The separation of the mobile solid magnetic phase support in all steps is achieved after adsorption of specific target compounds generally by using a magnetic separator with a predefined design or even a simple magnet block.

In a particular embodiment, the magnetic mobile solid phase support contains magnetic particles in the core and the surface coating is comprised of a mixture of different functional groups, which have two main functions: firstly, as a magnetic mobile solid phase support one for depletion or separation and on the other hand as a magnetic mobile solid phase support two for the specific isolation by positive selection of some compounds of interest from the trace compounds.

To carry out the process of the invention the abundant matrix compounds are bound to a magnetic mobile solid phase support such as an adsorbent of silica gel particles with or without at least one magnetic core and which may have functional groups such as —$NH_2$ and —COOH. In the embodiment, the silica particles have mesoporous structures ranging in size from 2 to 50 nm preferred from 5 to 30 nm and the inner surface of a range of 0.1 to 400 $m^2/g$, preferably from 10 to 200 $m^2/g$.

The mobile solid phase support contains silica particles which can be configured with at least one magnetic core. The doped silica with iron oxide cores includes a surface coating with functional groups such as —OH, —COOH, —$NH_2$, R—$SO_2$—OH, —$NH_2$; —RNH, —$R_2$N, alkyl such as $CH_3$, —$C_2H_5$, —$C_4H_3$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_6H_5$, —$ZrO_2$, $TiO_2$, $C_6H_9NO_6$, phenylhexyl, biphenyl, hydroxyapatite, boronic acid.

The functional groups mentioned above can vary in dependence of the target compounds to be depleted and/or analyzed. Normally the binding of trace compounds is reversible. But some of the functional groups from the particle surface may also induce an irreversible binding towards the compounds and/or trace compounds. Some effects ensure an optional reversible binding of the compounds and trace compounds on the surface of the magnetic mobile solid phase support. These effects include ionic exchange, hydrogen bonding, hydrophobic interactions, α-π interactions, and metal-ion interactions. The above mentioned interactions occur particularly when using special polar, organic solvents and aqueous acid, bases or salt solutions, leading to adhesion of the compounds of the sample for depletion and/or an adhesion of compounds and/or trace compounds on the surface of the magnetic mobile solid phase support.

The coating procedure of iron oxide-containing particles with a silica layer is state of the art as presented in the following two papers: (J. Colloid Interface Sci 1968, 26, 62-69; Langmuir 2005, 21, 10763-10769; J. Colloid Interface Sci 2005, 283, 392-396).

The coating of iron oxide-containing particles with a silica layer for the inventive method can be achieved for example as follows:

Iron oxide-containing particles are suspended in an alcohol (e.g. isopropanol) whereby the alcohol is added under vigorous stirring in the presence of ammonia for coating with a silica layer as result of hydrolysis of tetraethyl orthosilicate (TEOS). The thickness of the coating can be controlled by the amount of added TEOS.

The particles containing silica coated iron oxides are washed with an alcohol (e.g. methanol) within the cleanup step and stored in aqueous buffers including e.g. deionized water.

In a preferred embodiment of the invention the silica particles consist of a mesoporous $SiO_2$-layer which is applied to the magnetic core and has a layer thickness ranging from 10 nm to 100 nm.

Magnetic cores, e.g. iron oxide $Fe_2O_3$ or $Fe_3O_4$, of the inventive mobile solid phase support is embedded within silica gel preferably but also refers to polystyrene, melamine, polymethacrylate, polyamide, polyvinylchloride, polyethylene, polypropylene, polyester, polycarbonate, polyacrylamide, agarose, chitin, dextran, and polyvinylalcohol.

For the inventive process iron oxide particles are preferably used with a mesoporous silica coating as synthesized in the presence of polyethylene glycol as porogenic agents for example.

Preferably silica gel particles having a layer thickness in the range of 10 to 100 nm, wherein the magnetic cores are composed of maghemite and/or magnetite ranging by mass content between 30 and 95 wt % and contain an average diameter in the range of 20 nm to 500 microns, preferably from 200 nm to 10 microns, most preferably from 300 nm to 5 microns.

In general, the particles have a diameter in the range of 20 nm to 500 microns, preferably from 50 nm to 100 microns, more preferably from 100 nm to 10 microns.

In the present invention, protic and aprotic solvents are used for binding, depletion and/or separation. These solvents have a dipole moment in the range of 1.6 to 4.0 Debye, preferably from 1.69 to 3.96 Debye.

Suitable systems of solvents used within this invention to achieve the depletion of the abundant matrix compounds include for example, but not exclusively named: acetonitrile, ethanol, methanol, propanol, isopropanol, n-propanol, isobutanol and n-butanol, and also acetone, dimethyl sulfoxide (DMSO) and polyethylene glycol (PEG), $HNO_3$, $HClO_4$, $H_2SO_4$, HCl, $CF_3COOH$, $CCl_3COOH$, $CH3COOH$, CHOOH, NaOH, KOH and $NH_4OH$ alone or in combination with each other. These solvents can be added before or after depletion and/or separation step. Salts such as $(NH_3)_2SO_4$, $(NH_4)CH_3COO$, $ZnSO_4$, $MgSO_4$, $K_4$-$[Fe(CN)_6]$, $CuSO_4$, $AgNO_3$, NaCl, KCl, $MgCl_2$, $(CH_3COO)_2Pb$ and $FeCl_3$ as aqueous solution or/and aqueous/organic solutions can be also involved within depletion and/or separation steps either alone or in combination with each other.

The above mentioned solvents may be used singly or in mixture. The mixtures are for example set to alcohols such as ethanol and isopropanol in various proportions by weight or acetonitrile together with an alcohol such as isopropanol or ethanol or a combination of alcohols, such as ethanol and isopropanol with different proportions by weight, for example, with acetonitrile is part of the solvents.

For further purification and/or concentration of trace components an additional step can be carried out using nonpolar, aprotic solvents such as hexane that means a residue can be resumed by adding a suitable aprotic polar solvent such as methanol or acetonitrile.

The inventive method can be performed in the form that a selective and/or reversible binding of compounds is carried out by binding abundant compounds to a first mobile solid phase support with simultaneous isolation of particular trace compounds whereby the analytical compounds remain in the solution. This has the advantage that depending on the kind of compound which should be depleted a fast and selective isolation of trace compounds parallel by binding of abundant compounds to the magnetic mobile solid phase support can be carried out. The obtained trace compounds can then be subjected to a subsequent analysis.

It is also possible to bind abundant compounds to a magnetic mobile solid phase support and then the remaining solution the trace compounds gets in contact with second, specific magnetic mobile solid phase support as well. The second, specific magnetic mobile solid phase support may differ when compared to the one used to deplete the abundant compounds by size and type of functional groups, so that only certain compounds or trace compounds become bound to the surface of a second magnetic mobile solid phase support by a specific selective binding. The selective process binding step can be done simultaneously with the depletion of the abundant compounds in parallel or in a step-wise fashion. The trace analytical target compounds thus separated can then be subjected to a specific elution and a subsequent readout analysis.

The invention is providing solutions of binding of trace compounds to suitable magnetic mobile solid phase support and then a depletion of abundant compounds is carried out and as result the separation of the target compounds of the sample is then achieved by a selective elution step and at the end the representative sample is subjected to the analysis.

The depletion and separation of trace compounds and/or compounds can take place simultaneously or at different times what means that the process steps is variable depending on the type of components/compounds.

In a preferred embodiment of the inventive method the volume fraction of the biological sample to the solvents is determined in a range of 0.25:1 to 25:1 (v/v), whereby the separation or isolation of trace compounds and/or of compounds bound to the silica particles with at least one magnetic core is carried out with a magnetic separator.

The inventive method can, for example, be carried out with the following steps:

(1) resolve a dried biological sample with a reconstitution buffer,
(2) providing a liquid biological sample containing one or more substances like trace compounds as well as abundant compounds,
(3) adding the internal standards and calibrators and then contacting the liquid biological sample with a first kind of magnetic solid mobile phase support like magnetic silica gel particles with a magnetic core,
(4) incorporation of depletion solvents in predefined ratio,
(5) vortexing mixing and incubation of the mixture, wherein abundant compounds get adsorbed on the surface of particles,
(6) separating the magnetic particles by applying a magnetic field, and
(7) separation the supernatant containing one or more trace compounds in solution or suspension. Alternatively extracting one or more specific components and/or compounds like of trace compounds with a second kind of magnetic solid mobile phase support like magnetic silica gel particles from the sample by a positive selection, followed by elution of specific analytes and readout analysis.
(8) Optionally, drying of the supernatant or the elution liquid or evaporation of the solvent mixture at elevated temperature (50-85° C.) in the inert gas stream, and
(9) analyzing the one or more compounds and/or trace components using gel electrophoresis, UHPLC, HPLC, UPLC, LC/MS, LC-MS/MS, capillary LC, capillary electrophoresis UV/Vis, immunoassay detection and/or flow cytometry.

The binding and/or accumulation of the abundant compounds and/or trace compounds on the surface of the magnetic mobile solid phase support may be achieved by different binding mechanisms. It is possible that the interaction compounds retention involves various interactions between compounds and support surface, so that during a subsequent sample preparation process the bounded compounds trace analytical target compounds/components can be optionally easily detached from the surface of the magnetic mobile solid phase surface again. Such interactions ensure the reversible binding of compounds onto the surface, including ionic interactions, hydrogen bonds, hydrophobic interactions, $\pi$-$\pi$ interactions and metal ion interactions.

The interactions allow in particular the use of polar solvent-induced adhesion of the compounds onto the solid phase surface of the adsorbent. Targeted modification of pH's, the salt concentration/ionic strength, the polarity of the solvent-induced adhesion is designed in such a way that the most abundant non-analytically relevant compounds and/or those responsible for causing the matrix effects are irreversible removed/bound onto the surface whereas the trace analytical target compounds are left in the supernatant and/or specifically eluted from the magnetic mobile solid phase support prior analysis.

The inventive method also includes the combination of the selective isolation of the trace compounds and the depletion and/or separation of compounds of a sample. The combination is usually, but not exclusively, made in a two-step process. Herein, compounds are bound either by selective or non-selective binding to the solid phase support, and thus removed from the reaction mixture. In a further step, the trace analytical target components, as obtained by a induced separation by pH-control, salt-concentration or solvent polarity, become selectively and reversibly bound to another solid phase support and therefore enabling a concentration step by varying/changing the solvent used for the elution from the solid phase support.

The steps may take place simultaneously in a reaction vessel/vial, but also at different times and in two or more vessel/vials. In one embodiment of the invention, the inventive method can be carried out as part of an in-vitro diagnostic means of parallel or simultaneous determinations of abundant compounds and/or trace compounds according to the invention, wherein the determinations are carried out at least for one patient sample. In a further embodiment of the invention, the inventive method can be carried out by means of a 2D-electrophorensis, wherein in the first dimension, isoelectric focusing, gel electrophorensis is performed in the second dimension.

In a further embodiment, the inventive method and its provisions can be carried out by means of a rapid test (e.g. lateral flow test), whether in single or multi-parameter determination.

Furthermore, the invention encompasses a fluid sample for chemical analysis and diagnostic preparation obtained from dried or fluid biological samples for chemical analysis and/or diagnostic purposes. Finally, the present invention includes the use of a microfluidic device for concentrating compounds like trace compounds from a biological sample for chemical analysis and diagnostic preparation wherein the use is composed of a cartridge which temporarily provided with or without a membrane to achieve a separation of the absorbent body unit from the hollow cartridge. The adsorbent body unit may comprise a filter paper, a capillary pipette tip or a modified polymeric sintered filter body and it can be attached to the end of the cartridge with a pipette tip-like geometry.

Some typical examples of the method of the invention are exemplified for various sample preparation applications. The invention is specified by the means of the following examples:

EXAMPLE 1

Determination of Vitamin D and its Metabolites in Serum Samples

TABLE 1

Specifications for a working prototype that complies to pre-defined specifications for healthy patients, state of the art LCMS/MS equipment on controlled samples.

| Vitamin D metabolite | Detection range |
| --- | --- |
| 25-OH vitamin D2 | 10-100 µg/L |
| 25-OH vitamin D3 | 10-100 µg/L |
| 1,25-(OH)$_2$ vitaminD3 | >25 µg/L |
| 3 epi 25-OH vitamin D3 | >25 µg/L |
| 24,25-(OH)$_2$ vitamin D3 | >25 µg/L |

Materials and Reagents

MagSiMUSDPREP Particle Mix
Organic Precipitation Reagent I (OPR I)
Reconstitution buffer for internal standard
Additional reagents supplied by user:
Deuterated Internal Standard: 25OH-Vitamin D3-d6 (Sigma Aldrich)
Reference material: 25OH-Vitamin D3; 1.25(OH)$_2$-Vitamin D3; Vitamin D3 (Sigma Aldrich)

Materials

Magnetic separator: MM-Separator M12+12 (Art.No.: MD90001)
Sample containers: 2 mL microtubes, brown HPLC vial (2 ml)
Micropipettes: 10-100 µL, 20-200 µL and 100-1000 µL

Protocol

1. Transfer 50 µL patient serum, control or calibrator to a 2 mL microtube
2. Add 20 µL Internal Standard solution to the sample
3. Add 40 µL MagSiMUS-DPREP Particle Mix and mix by pipetting
4. Add 260 µL OPR I and mix by 10 aspiration and dispensing cycles
5. Place the samples on the magnetic separator and incubate for 2 minutes until the supernatant is clear.
6. While avoiding contact with the pellet, transfer 80 µL of the supernatant to a HPLC vial for injection (5 µL).

Analytical Methods

To quantify 25OH-vitamin D3 and 1.25 (OH)$_2$-vitamin D3 in serum, an analytical assay was developed. A LC-MS/MS system (Shimadzu 8050) was used and calibrated to perform the measurements. Serum samples were spiked with 20 µg/L 25OH-vitamin D3 and 1.25(OH)2-vitamin D3, which is for 25OH-vitamin D3 within the stated concentration of 10-100 µg/L and for 1.25(OH)$_2$-vitamin D3 even below the stated concentration of >25 µg/L.

LC-MS/MS set-up
UPLC: Nexera X2 UHPLC
Analytical column: Phenomenex Kinetex 2.6µ F5, 100×3 mm
(cat #00D-4723-Y0)
Mobile Phase A: ddH$_2$O, 0.1% formic acid
Mobile Phase B: MeOH, 0.1% formic acid
Pumping mode: Binary Flow
Column oven: 40° C.
Pump B %: 65%
Total flow: 0.75 mL/Min.
Injection volume: 5 µl (up to 50 µl possible)
MS: Shimadzu LCMS-8050, Source: APCI, Mode: MRM (+), Dwell time: 100 msec, Interface Temp.: 350° C., Nebulizing Gas flow: 4.4 L/min

TABLE 2

Retention time and MS settings

| Parameter | Retention time (min) | Q1 (m/z) | Q3 (m/z) | Q1 Pre Bias (v) | CE (V) | Q3 Pre Bias (v) |
| --- | --- | --- | --- | --- | --- | --- |
| 1,25(OH)$_2$—Vitamin D3 | 3.05 | 399.1 | 135.1 | −19 | −21 | −26 |
| 25OH—Vitamin D3-d6 (internal standard) | 3.66 | 389.2 | 371.4 | −19 | −15 | −28 |
| 25OH—Vitamin D3 | 3.66 | 383.6 | 257.2 | −19 | −15 | −28 |
| Vitamin D3 | 4.83 | 385.1 | 259.2 | −11 | −16 | −30 |

Results

To evaluate the MagSiMUSD$^{PREP}$ kit, both in-house measurements as well as measurements at partner labs were done.

In-House Measurements

The concentration of Vitamin D, 25OH-vitamin D3, 1.25 (OH)$_2$-vitamin D3 and the internal standard 25OH-Vitamin D3-d6 could be measured accurately on the LC-MS/MS system. No binding to the beads has been observed, so removal from the sample, could be detected. The recovery of the spiked vitamins was above 95%. The analytical method for measuring the other 3 compound mentioned in table 1 is currently under development. Standard material was not available at the time, therefore the settings of the LC-MS/MS system could not be optimized. The successful measurement of 25OHvitamin D3 and 1.25(OH)$_2$-vitamin D3 however provides a good indication that the other vitamin D metabolites can also be measured and no loss in recovery will occur.

Internal Standard Analysis

Internals standard solution spiked in either phosphate buffered saline (PBS) or serum (20 µg/L 25OH-Vitamin D3-d6) was measured to test recovery of the sample prep process. PBS is a buffer which only contains salts and no proteins so it could be used to determine maximal signal and test the removal of potentially matrix effect-causing components in the serum sample.

TABLE 3

Results of PBS and serum sample spiked with internal standard

| Nr. | Sample (Matrix) | Internal standard | VitD sample prep | Injection volume (μl) | Peak area (AU) |
|---|---|---|---|---|---|
| 1 | PBS | YES | NO | 5 | 7360 |
| 2 | PBS | YES | YES | 5 | 7671 |
| 3 | PBS | YES | YES | 10 | 15767 |
| 4 | Serum | YES | YES | 10 | 14608 |
| 5 | Serum | YES, 2x diluted | YES | 10 | 7518 |

Concluding Remarks

25OH-Vitamin D3-d6 shows no unwanted binding to MagSiMUS-$D^{PREP}$ Particle Mix (Nr. 1/2)→recovery 104%

Doubling the injection volume is doubling the peak area (Nr. 2/3)→method is linear Matrix impact (ion suppression) is very limited (Nr. 3/4)→calculated matrix effect is 92%

Method is scalable (Nr. 1-5)

Measurement on Variation

To assess the reproducibility of the sample preparation method, serum was spiked with internal standard (25OHVitamin D3-d6, 20 μg/L) and 3 separate sample preparations and analysis were performed. The coefficient of variation was 4.7%, which is below the commonly excepted range of 10-15% (table 1).

TABLE 4

Results of repeated measurements of internal standard in serum

| Measurement | Sample | Peak area |
|---|---|---|
| 1 | Serum spiked with 25OH-Vitamin D3-d6 | 15767 |
| 2 | Serum spiked with 25OH-Vitamin D3-d6 | 14520 |
| 3 | Serum spiked with 25OH-Vitamin D3-d6 | 14608 |
| Average | | 14965 |
| CV | | 4.7% |

Analysis of Spiked Serum

Serum samples were spiked with 20 μg/L internal standard (25OH-Vitamin D3-d6), 25OH-Vitamin D3, 1.25 (OH)$_2$-Vitamin D3 and Vitamin D3 to evaluate the newly developed LC-MS/MS method and test the MagSiMUS $D^{PREP}$ kit. Peak areas of all 4 analyses were above 10.000 units. Limit of detection is typically between 100-500 units.

TABLE 5

Results of measuring 4 vitamin D metabolites

| Analyte | Peak area (average from three measurements) |
|---|---|
| 25OH-Vitamin D3-d6 | 14965 |
| 25OH-Vitamin D3 | 10200 |
| 1,25(OH)$_2$ Vitamin D3 | 16455 |
| Vitamin D3 (cholecalciferol) | 70815 |

Vitamin D Measurements on Site at a Partner

The vitamin D sample preparation method was also evaluated on site at a partner. The metabolites 25OHVitamin D3, 25OH-Vitamin D2, 25OH-3epi-Vitamin D3, and 24.25 (OH)$_2$-Vitamin D3 could be measured with similar results as their reference method (accuracy 83-105%).

TABLE 6

Vitamin D metabolites. Vitamin D total is the sum of: 25OH-Vitamin D3; 25OH-Vitamin D2; 25OH-3epi-Vitamin D3; and 24,25(OH)$_2$-Vitamin D3

| | 25-OH Vitamin D3 (ng/ml) | | Vitamin D total (ng/ml) | |
|---|---|---|---|---|
| Sample | Reference method | MMD method | Reference method | MMD method |
| 1 | 23.9 | 22.4 | 29.6 | 26.4 |
| 2 | 7.1 | 6.0 | 8.1 | 6.8 |
| 3 | 33.9 | 35.8 | 39.3 | 41.3 |
| 4 | 14.6 | 13.4 | 17 | 14.01.15 |

Due to the sensitivity limits of the triple quadrupole LC-MS/MS system with a limit of quantification (LOQ) of ~1 ng/ml only the total sum concentration of the four metabolites rather than the individual concentrations could be detected (table 6).

EXAMPLE 2

Analysis of Thiamine Diphosphate and Pyridoxal-5'-Phosphate (Vitamin B1 and B6) in Whole Blood Using the UHPLC/MS-8050 and the MagnaMedics MagSiMUS-$B^{PREP}$ Kit Introduction Vitamin B1, thiamin, plays an important role in the metabolic pathway in the human body. The biological active form is Thiamine diphosphate (TDP). The water soluble vitamin acts as a coenzyme for the enzymatic degradation of glucose in the citric acid cycle. A non-varied diet or malnutrition can quickly lead to a deficiency which can result in inter alia depression, muscle weakness and tachycardia. Vitamin B6 has multiple forms. The biological active form in the human cell is Pyridoxal-5'-phosphate (PLP). The water soluble vitamin acts as a coenzyme in the formation of amino acids, amines and peptides. In case of a deficiency the other B vitamins will also be deficient. A PLP deficiency can occur due to chemotherapy, alcoholism, pregnancy and kidney failure. To this day these two vitamins (TDP and PLP) are predominantly analyzed with HPLC and fluorescence detection. These methods are performed with excessive sample preparation including pre- or postcolumn derivatization using toxic reagents and have relatively long runtimes. Due to the rising numbers of patient samples in clinical laboratories there is need for a simple and fast chromatographic method without excessive sample preparation. The aim of this study was therefore to set up a simple and fast UHPLC method with mass spectrometric detection, with minimal sample preparation, resulting in a total solution.

Method

Sample Preparation

From whole blood samples, calibrator or control samples only 50 μl of sample was transferred to a 96-well microtiter plate which was positioned above a magnet. 10 μL of internal standard mix (containing d3-TDP and d3-PLP) and 40 μL MagSiMUS-B$^{PREP}$ bead mix (MagSiMUSTDM$^{PREP}$ type 2) was added to the sample and mixed. The proteins were precipitated by the addition of 100-200 μL precipitation solution such as between 6 and 10% (v/v) perchloric acid (PCA) in DD water followed by intense aspiration and dispensing of the mixture. After magnetic separation 90 μL of the supernatant was transferred to a HPLC vial and mixed with acetonitrile.

LC-MS/MS Analysis

10 μL of the supernatant was analyzed on a Nexera X2 binary UHPLC system (Shimadzu, Japan) and coupled to a tandem quadrupole mass spectrometer (LCMS-8050, Shimadzu, Japan). TDP was measured with MRM transition 424.9>122.2 and PLP with MRM transition 247.9>150.0. For both compounds two reference ions were measured simultaneously and the ratio between the main transition and the reference transitions was established and set in the method. The deuterated internal standards were measured with MRM transitions 427.9>125.2 (d3-TPP) and 250.9>153.0 (d3-PLP).

TABLE 1

Summary of the UHPLC parameters

| UHPLC method | |
|---|---|
| Column | Phenomenox F5, 100 × 3 mm, 2.6 μm |
| Column temperature (° C.) | 15 |
| Mobile phase | A: Acidified H$_2$O |
| | B: CH$_3$CN |
| Injection volume (μL) | 10 |

TABLE 2

Summary of the MS/MS parameters

| MS/MS method | |
|---|---|
| Nebulizer gas (L/min) | 2 (N$_2$) |
| Heating gas (L/min) | 10 (Air) |
| Drying gas (L/min) | 5 (N$_2$) |
| Interface temperature (° C.) | 300 |
| Desolvatation line (° C.) | 250 |
| Heat block temperature (° C.) | 400 |
| Interface voltage (kV) | 4 |
| Dwell time (ms) | 30 |
| Pause time (ms) | 3 |
| Ionization | ESI positive |
| Scan Type | MRM |

Results and Discussion

Method Results

Both compounds showed excellent linearity (r2>0.999) in a clinically relevant concentration range (TDP: 11.8-1176 nmol/L; PLP 20.2-2023 nmol/L). The LOD and LOQ were 2.7 nmol/L and 8.2 nmol/L for TPP, respectively and 0.6 nmol/L and 1.8 nmol/L for PLP.

TABLE 3

Overview on the obtained results

| Compound | Target (T)/Internal Standard (I) | MRM Quantifier | MRM Quantifier 1 | MRM Quantifier 2 | Retention time (min) |
|---|---|---|---|---|---|
| TDP | T | 424.9 > 122.2 | 424.9 > 304.0 | 424.9 > 81.1 | 1.60 |
| PLP | T | 247.9 > 150.0 | 247.9 > 94.1 | 247.9 > 122.05 | 1.79 |
| d$_3$-TDP | I | 427.9 > 125.2 | — | — | 1.63 |
| d$_3$-PLP | I | 250.0 > 153.0 | — | — | 1.82 |
| Compound | Target (T)/lnternal Standard (I) | MRM Quantifier | MRM Quantifier 1 | MRM Quantifier 2 | Retention time (min) |

| Compound | Concentration (nm/L) | SD | % RSD |
|---|---|---|---|
| TDP | 11.8 | 0.74 | 6.2 |
| | 276 | 15 | 5.6 |
| | 1176 | 32 | 2.6 |
| PLP | 20.2 | 1.4 | 6.8 |
| | 443 | 25 | 5.6 |
| | 2023 | 113 | 5.7 |

Conclusions

The developed method with simple and fast sample preparation is an appropriate method for detection of TDP and PLP in whole blood samples.

Both compounds, TDP and PLP showed excellent linearity ($r^2>0.999$) in a clinically relevant range.

Full sample preparation for a 96 well plate takes 30 minutes, total runtime on the LCMS/MS is 3 minutes per sample.

Due to the fast and automated sample pretreatment and short analysis time this total solution is applicable for a high number of patient samples offered at clinical laboratories.

The cost per sample is relatively low in comparison to accepted standard methods, due to the limited sample pretreatment without centrifugation, short run times and no need for expensive reagents.

EXAMPLE 3

Oral Anticoagulants Monitoring in Plasma Sample

Introduction

In this study we compared manual sample preparation of plasma samples containing the anticoagulants apixaban, edoxaban, dabigatran and rivaroxaban using MagnaMedics MagSiMUS-TDM$^{PREP}$ Type II kit vs automated sample preparation (same kit) processing the plasma sample on an automated working platform underlying Hamilton Bioanalytical STARlet. All four mentioned anticoagulants have been analyzed in parallel in a multianalyte set-up. Time consuming centrifugation steps have been omitted in both cases; manual and automated sample preparation.

Even though with the manual sample preparation method already a good linearity of the calibration curve could be observed (regression values between $r^{2=0.993}$ and $r^2=0.997$) the linearity could be significantly enhanced for the automated sample preparation method (all parameters showed regression values >0.998). However the correlation between manually prepared selected plasma patient samples and samples prepared by the Hamilton Bioanalytical STARlet at various rivaroxaban concentrations were found to be close at $r^2=0.993$ between a concentration range of 5-400 μg/L. Chromatographic separation was achieved by a Hypersil Gold C18 column from Thermo Fisher Scientific and the analytical read-out has been performed on Thermo Fisher Scientific TSQ Vintage triple quadrupole mass spectrometer.

Medical Background

The non-vitamin K antagonists anticoagulants (NOACs: New oral anticoagulants) apixaban, edoxaban, dabigatran and rivaroxaban have emerged as alternative to vitamin K antagonists (VKAs), like Warfarin for the medical management of thromboembolic diseases. NOACs provide highly selective modes of action: dabigatran acts selectively as thrombin (FIIa) inhibitor, whereas apixaban, rivaroxaban and edoxaban directly inhibit factor Xa. In principle monitoring of NOACs can be addressed by either functional tests, like calibrated chromogenic anti-Xa assays for rivaroxaban and apixaban or by liquid chromatography mass spectrometry (LC-MS/MS), which is valued as "gold-standard" for quantitative drug analysis.

Chemicals and Reagents

Pure substances of apixaban, dabigatran, rivaroxaban and edoxaban were purchased from Molekula (Munich, Germany). Internal standards [$^{13}$C, $^2$H$_7$]-apixaban, [$^{13}$C$_6$]-dabigatran, [$^{13}$C$_6$]-rivaroxaban and [$^2$H$_6$]-edoxaban were obtained from Alsachim (Illkirch, Grafenbstaden, France). Acetonitrile and formic acid in LC-MS quality were purchased from VWR.

Manual Plasma Sample Preparation Using MagSiMUS-TDM$^{PREP}$ Kit

Plasma sample have been deproteinated and cleaned-up from ion suppression causing compounds using the MagnaMedics MagSiMUS-TDM$^{PREP}$-Type II kit. All samples have been prepared in 2 ml, cylindrical shaped centrifuge tubes to ensure proper bottom/side collection using MagnaMedics M12+12 magnetic separator. The sample preparation has been performed as described in the MagSiMUS-TDM$^{PREP}$ Type II manual, except that the samples have been vortexed for 10 sec. instead of pipette mixing, in brief: 50 μl plasma sample (patient sample, QC or calibrant) have been placed in a centrifuge tube. 20 μl Internal standard mix diluted to a working solution of 100 μg/ml in OPR I (Organic precipitation reagent I) has been added, followed by addition of 40 μl homogenized magnetic bead suspension and 130 μl acetonitrile (ACN). The reaction mix has been vortexed mixed for 10 s and then placed on the M12+12 magnet for a 1 min separation. 80 μl supernatant has been transferred in a HPLC glass vial.

Manual Plasma Sample Preparation Protocol Using ACN Deproteination Followed by Centrifugation 50 μl plasma were precipitated by addition of 100 μl ACN in a standard centrifuge tube. After 30 s vortexing the reaction mix has been centrifuged at 4° C., 15,000 g for 10 min.

Automated Plasma Sample Preparation on Hamilton Bioanalytical STARlet

LC-MS/MS Conditions

The chromatographic separation has been achieved using Hypersil Gold C18 column from Thermo Fisher Scientific (50*2.1 mm, 1.9 μm particle size). The flow rate was set to 350 μL/min. The mobile phase consisted of 100% ACN (A) and ultrapure water containing 0.1% formic acid (B). The following gradient has been used for separation:

TABLE 1

| LC conditions | |
|---|---|
| Time | Percentage A |
| 0-0.5 min. | 15.00% |
| 0.5-0.7 min. | Linear from 15% to 85% |
| 0.7-1.8 min. | 85.00% |
| 1.8-2 min. | Linear from 85% to 15% |
| 2-2.5 min. | 15.00% |

Then the samples were analyzed on a Thermo Fisher Scientific TSQ Vintage triple quadrupole mass spectrometer using selected reaction monitoring (SRM) mode and positive electrospray ionization. Settings were 3 kV spray voltage, 350° C. vaporizer temperature and 300° C. heated capillary temperature. Argon was used as collision gas and the pressure was set to 1.5 mTorr.

The system has been equipped with an Accelera 1250 pump and Accelera autosampler using tray and column temperature between 23 and 30° C. Injection volume was 5 µl (partial loop) of the extracted plasma samples.

Stock Solutions, Calibration Standards, and Quality Controls

The deuterated internal standards have been dissolved in acetonitrile and have been 8.3-fold diluted in OPR I of MagnaMedics to a final concentration of 240 µg/L.

Automated Sample Preparation

The automated sample processing on a liquid handling platform has been performed on a Hamilton Bioanalytical STARlet platform. This platform has a couple of features, which makes this system a) specially suitable for the use in routine bioanalytical diagnostics lab and b) for use with magnetic beads, like in the MagSiMUS-TDM$^{PREP}$ kit.

The process is as following:
(i) Automated pre-configuration→dilution of IS; dilutions for Cals and QCs
(ii) Transfer 50 µl serum to MTP plate
(iii) Enter sample type (serum/plasma/whole blood), in this case plasma in software
(iv) Start the application.

A full 96 well MTP for plasma samples is processed within 25 minutes using the 4-span robotic arm. Labor time savings are as following:

TABLE 3

Comparison overview between methods

| Sample prep comparison | MagSiMUSTDM$^{PREP}$ processed on Hamilton Bioanalytical STARlet | MagSiMUSTDM$^{PREP}$ processed manually | Reference acetonitrile PPT protocol |
|---|---|---|---|
| Total protocol time per sample | 3 min. | 3 min. | 12 min. |
| Time for 96 samples | 25 min. | 50 min. | 75 min.* |
| Hands on time | 10 min. | 50 min. | 50 min. |

*Using standard 24 tube centrifuge

Results

LC-MS/MS Data

Comparing two manual methods—the MagSiMUS-TDM-$^{PREP}$ magnetic bead based sample preparation method and a simple acetonitrile PPT method followed by centrifugation comparable peak shapes have been seen for apixaban, dabigatran and rivaroxaban. For edoxaban at 2 µg/L edoxaban concentration spiked to blank plasma, also symmetrical chromatogram peaks have been observed for both sample preparations—the magnetic bead and centrifugation methods.

TABLE 2

MS transitions for the target parameters
(i.e. apixaban, dabigatran, rivaroxaban)

| Analytical Parameter | Quantifier | Qualifier |
|---|---|---|
| apixaban | M/z 460.2 → 443.2 | M/z 460.2 → 199.1 |
| dabigatran | M/z 472.2 → 289.1 | M/z 472.2 → 144.1 |
| rivaroxaban | M/z 436.1 → 231.1 | M/z 436.1 → 231.1 |

Linearity could be demonstrated over the entire concentration range of 2_500 µg/L. Using MagSiMUS-TDM$^{PREP}$ sample preparation kit in manual fashion regression values of r2>0.993 have been observed.

Comparing manual versus automated sample preparation the linearity significantly improved for the automated liquid handling process.

TABLE 4

Comparison overview between manual sample preparation and automated sample preparation method on the Hamilton Bioanalytical STARlet using MagSiMUS-TDM$^{PREP}$

| Parameter | Manual sample preparation | Automated sample preparation on the Hamilton Bioanalytical STARlet |
|---|---|---|
| Apixaban | $R^2 = 0.996$ | $R^2 = 0.999$ |
| Dabigatran | $R^2 = 0.997$ | $R^2 = 0.999$ |
| Edoxaban | $R^2 = 0.993$ | $R^2 = 0.998$ |
| Rivaroxaban | $R^2 = 0.993$ | $R^2 = 0.999$ |

Concluding Remarks

In this study we compared two manual plasma sample preparation methods for plasma samples containing NOACs—a) a simple acetonitrile protein precipitation method (PPT) followed by centrifugation and b) the MagSiMUS-TDM$^{PREP}$ magnetic bead based method. Secondly the magnetic bead based method has been investigated in manual and automated sample preparation fashion using Hamilton Bioanalytical STARlet.

Some time savings can be already achieved with MagSi-MUS-TDM$^{PREP}$ in a manual fashion. However, sample preparation by an automated liquid handling system in combination with a magnetic bead based sample preparation gives the most labor time saving effect. Additionally the read-out data quality—expressed as linear regression values—can be significantly enhanced using MagSiMUS-TDM$^{PREP}$ in combination with an automated liquid handling sample preparation process.

EXAMPLE 4

Sample Preparation for Determination of Nicotine in Serum

Materials

Serum sample
MagSiMUS-TDM$^{PREP}$ type I; 50 mg/ml
Organic Precipitation Reagent (OPR/ACN containing 0.05% HCl 0.1N)
Centrifuge tube; 2 ml
MM separator M12+12
Pipettes
Microplate reader
Microplate 96 well Protocol 1. Transfer 100 µl of serum sample in a 2 ml centrifuge tube
2. Add 50 µl of a bead mix as MagSiMUS-TDM$^{PREP}$ type I
3. Mix the sample by pipetting up and down 5 times
4. Add 600 µl OPR to the sample (ratio 1:4 aqueous phase/organic phase) and mix the sample by pipetting up and down 5 times
5. Incubate it for 1 min at RT
6. Collect the beads using the MM separator M12+12
7. Transfer 400 µl of the supernatant to a new centrifuge tube
8. Measure the OD at 259.5 nm Read out: OD at 259.5 nm on microplatereader
Spiked nicotine in sample:
A series of nicotine samples with various concentrations as 0.05, 0.1, 0.20, 0.5, 2.0 ppm (mg/ml) were spiked in serum.

TABLE 1

OD values measured at 259.5 and recoveries

| Sample | 0.05 ppm | 0.1 ppm | 0.2 ppm | 0.5 ppm | 2 ppm |
|---|---|---|---|---|---|
| OD/259.5/ reference (nm) | 0.43 | 0.80 | 0.85 | 2.01 | 3.93 |
| OD/259.5/ processed with sample prep protocol (nm) | 0.34 | 0.48 | 0.61 | 1.36 | 3.21 |
| Recovery (%) | 79.0 | 60.0 | 70.7 | 67.0 | 81.7 |

Then, the samples are handled according to the above sample preparation protocol and measured for OD at 259.5 nm. The recovery of nicotine when the sample preparation protocol is applied is used as process parameter.

An overall recovery between 60 and 80% is obtained. We do recommend to use another analytical techniques for the quantification (e.g. LC-MS/MS and to use an internal standard in order to correct the determined concentrations in respect to its recovery.

EXAMPLE 5

Sample Preparation for Determination of Chloramphenicol in Milk

Materials

Reconstituted milk sample
MagSiMUS-TDM$^{PREP}$ type 1; 50 mg/ml
Organic Precipitation Reagent (OPR/100% acetonitrile)
Centrifuge tube; 2 ml
MM separator M12+12
Pipettes
Microplate reader
Microplate 96 well Protocol 1. Transfer 100 µl of serum sample in a 2 ml centrifuge tube
2. Add 50 µl of Bead mix as MagSiMUS-TDM$^{PREP}$ type 1. Mix the sample by pipetting up and down 5 times.
3. Add 250 µl OPR to the sample and mix the sample by pipetting up and down 5 times.
4. Incubate it for 1 min at RT
5. Collect the beads using the MM separator M12+12
6. Transfer 300 µl of the supernatant to a new centrifuge tube
7. Measure the OD at 278 and 405 nm Readout: OD at 405 and 278 nm on microplate reader
The clean-up of the sample preparation process was evaluated on a triplicate sample (M1, M2 and M3). Positive control sample: milk sample diluted 1:100 with DD water. Negative control sample: DD water: acetonitrile 1:1.

TABLE 1

Summary results on cleaning up samples by removing proteins

| Sample | Milk diluted 1:100 | DD water/ Acetonitrile | M1 | M2 | M3 |
|---|---|---|---|---|---|
| OD (405 nm) | 0.330 | 0.031 | 0.048 | 0.048 | 0.049 |
| OD (278 nm) | 0.889 | 0.080 | 0.588 | 0.661 | 0.767 |

The OD measurements at 405 nm shows that the clean-up process on milk samples using MagSiMUS-TDM$^{PREP}$ sample preparation technology platform is very effective; approximately 99.5% of the colloidal proteins are removed and leaving in supernatant the non-protein analytic targets as measured by OD at 278 nm.

Spiked chloramphenicol sample; a series of chloramphenicol samples with various concentrations as 0.1, 0.25, 0.5, 1.0, 2.0 ppm (mg/ml) were spiked in DD water.

TABLE 2

Summary results on OD values and recoveries

| Sample | 0.1 ppm | 0.25 ppm | 0.5 ppm | 1 ppm | 2 ppm |
|---|---|---|---|---|---|
| OD/278/reference (nm) | 0.23 | 0.52 | 0.75 | 1.48 | 2.79 |
| OD/278/processed with sample prep protocol (nm) | 0.24 | 0.53 | 0.58 | 1.36 | 2.72 |
| Recovery (%) | 104.340 | 101.900 | 77.333 | 91.890 | 97.490 |

Then, the samples are handled according to the above sample preparation protocol and measured for OD at 278 nm. The recovery of chloramphenicol when the sample preparation protocol is applied is used as process parameter.

EXAMPLE 6

Sample Preparation for Determination of Glutathione (GSH) in Serum

Materials

Serum sample/Bovine
MagSiMUS-TDM$^{PREP}$ type 1; 50 mg/ml
Organic Precipitation Reagent (OPR/Acetonitrile 100%)
Centrifuge tube; 2 ml
MM separator M12+12
Pipettes
Microplate reader
Microplate 96 well Protocol 1. Transfer 100 µl of serum sample in a 2 ml centrifuge tube
2. Add 50 µl of Bead mix as MagSiMUS-TDM$^{PREP}$ type I. Mix the sample by pipetting up and down 5 times.
3. Add 600 µl OPR to the sample (ratio 1:4 aqueous phase/organic phase) and mix the sample by pipetting up and down 5 times.
4. Incubate it for 1 min at RT
5. Collect the beads using the MM separator M12+12
6. Transfer 400 µl of the supernatant to a new centrifuge tube
7. Measure the OD at 280 nm.

Read out: OD at 280 nm on microplate reader
Spiked Glutathione in serum sample:
A series of glutathione samples with various concentrations as 0.20, 0.5, 2.0 ppm (mg/ml) were spiked in serum. Glutathione stock solution was 10 ppm.

TABLE 1

Summary results on OD values and recoveries

| Sample | 0.2 ppm | 0.5 ppm | 2 ppm |
|---|---|---|---|
| OD/280/reference (nm) | 0.20 | 0.31 | 0.43 |
| OD/280/processed with sample prep protocol (nm) | 0.18 | 0.24 | 0.40 |
| Recovery (%) | 90.0 | 77.4 | 93.0 |

Then, the samples are handled according to the above sample preparation protocol and measured for OD at 259.5 nm. The recovery between 77 and 93% was obtained which proved that the method can be transferred to LC-MS/MS systems in order to obtain more accurate results.

EXAMPLE 7

Sample Preparation Method for Determination of Melamine in Milk

Materials

Reconstituted milk from dried powder
MagSiMUS-TDM$^{PREP}$ type I; 50 mg/ml and MagSi-proteomics C4, C8, C18 bead mix/1:1:1/10 mg/ml; ratio 4:1
Organic Precipitation Reagent (OPR/100% Acetonitrile)
Centrifuge tube; 2 ml
MM separator M12+12
Pipettes
Microplate reader
Microplate 96 well
Read out: OD at 405 and 240 nm on microplatereader
The clean-up of the sample preparation process was evaluated on a triplicate sample (M1, M2 and M3)
Positive control sample: milk sample diluted 1:100 with DD water
Negative control sample: DD water: acetonitrile 1:1

TABLE 1

Summary results on cleaning up milk samples by removing proteins

| Sample | Milk diluted 1:100 | DD water/ Acetonitrile 1:1 | M1 | M2 | M3 |
|---|---|---|---|---|---|
| OD (405 nm) | 0.33 | 0.031 | 0.048 | 0.048 | 0.049 |
| OD (240 nm) | 0.889 | 0.080 | 0.550 | 0.563 | 0.572 |

The OD measurements at 405 nm shows that the cleanup process on milk samples using MagnaMedics bead based sample preparation technology platform is very effective; approximately 99% of the colloidal proteins are removed and leaving in supernatant the non-protein analytic targets as measured by OD at 240 nm.

Spiked melamine sample:
A series of melamine samples with various concentrations as 0.05, 0.1, 0.20, 0.5, 2.0 ppm (mg/ml) were spiked in DD water.

TABLE 2

Summary results on OD values and recoveries

| Sample | 0.05 ppm | 0.1 ppm | 0.2 ppm | 0.5 ppm | 2 ppm |
|---|---|---|---|---|---|
| OD/240/reference (nm) | 0.12 | 0.15 | 0.21 | 0.38 | 1.16 |
| OD/240/processed with sample prep protocol (nm) | 0.11 | 0.14 | 0.19 | 0.35 | 0.99 |
| Recovery (%) | 94.2 | 92.0 | 90.0 | 92.6 | 85.6 |

Then, the samples are handled according to the above sample preparation protocol and measured for OD at 240 nm. The recovery of melamine when the sample preparation protocol is applied is used as process parameter.

EXAMPLE 8

Reconstitution Method for Dried Biological Samples—Tip/Absorbent Body Unit

Preparation of the Absorbent Body Unit for Coating and Filling the Body Filter with PVP 360 (0.5 wt/v %) and Span 80 (0.5 wt/v %) for Blood Uptake 1. Pre-wash the filter/absorbent material with bicarbonate buffer (pH 8.5) for 10 min at RT under rotation in a 50 ml centrifuge tube. Then rinse the filter/absorbent material with DD water 3× for 5 min each time at RT under rotation.
2. Prepare PVP, 10, 300 and Span-80, Na2 EDTA, Na citrate solutions such 0.5 wt % in DD water.
3. Soak the filter/absorbent materials for 8 h in PVP/Span-80/Na2 EDTA solutions mix (0:99:1) and 40:50:10 under rotation in a 50 ml centrifuge tube
4. Rinse/No rinse the treated body filter materials with DD water 3×/1 h each time under/RT.
5. Dry out the body filter materials on a paper tissue at RT overnight.

The absorbent body unit uptake is in the range between 5 and 100 µl and preferably between 15 and 75 µl. It can be fine tuned using the adsorption coefficient of the modified sintered porous material with the hydrogel coatings which is given in this example.

Concerning the pre-defined volumes for the reconstitution of dried sample one can use pre-defined volumes between 3× and 20× adsorption volume of the absorbent body unit, most preferred between 3× and 10×. The greater the reconstitution buffer volume used the greater the dilution factor introduced. At the end of the process from the reconstitution sample volume has to be subtracted the dead volume of the adsorbent body that will also accommodate reconstituted sample that will stay in it.

When it is used low pre-defined reconstitution buffer composition (e.g. 3×), the dilution factors introduced are smaller but also in a adsorbent unit will be kept due to the dead volume more concentrated in the reconstituted sample. Therefore these pre-defined volumes are application driven.

Blood Uptake and Release Experiments and Blood Uptake

In order to determine the blood uptake a series of filter/absorbent samples were weighed in using an analytical balance (Sartorius).

The aim of this experiment was to determine the specific absorption coefficient as defined by the ratio between the mass of absorbed blood/mass of absorbent material, as in the last column of the table 1. The uptake is achieved by contacting the absorbent material with the whole blood sample for ca. 5-6 s. After that the absorbent materials filled with blood is let to dry out at RT for 8 h (overnight).

TABLE 1

Summary results on blood uptake

| No | Filter/absorbent mass (g) | absorbent + blood (g) | Blood uptake (g) | Blood mass/absorbent mass (specific absorption coefficient) |
|---|---|---|---|---|
| 1 | 0.011 | 0.023 | 0.012 | 1.091 |
| 2 | 0.026 | 0.051 | 0.025 | 0.961 |
| 3 | 0.033 | 0.069 | 0.036 | 1.090 |
| 4 | 0.049 | 0.093 | 0.044 | 0.898 |
| 5 | 0.057 | 0.128 | 0.071 | 1.245 |
| 6 | 0.075 | 0.142 | 0.067 | 0.893 |

The average specific absorption coefficient is 1.030, as obtained taking the six masses of the absorbent body units ranging from 0.011 to 0.075 g.

Blood Sample Release

In order to evaluate the blood release out of the filter/absorbent material the below work protocol was considered. The release was focused on the blood sample recovery out of the dry filter/absorbent material after an imposed contact time between sample and DD water for 10 min.

Work Protocol

Transfer the absorbent body material to a 2 ml plastic centrifuge tube.
Add to the body absorbent containing the equivalent of 20, 30 and 50 µl dried whole blood, a predefined volume of 500 µl DD water as reconstitution buffer to each sample. Then, the body absorbent is kept in contact with DD water for 10 min under rotation at RT. Transfer 100 µl from each reconstituted dried blood sample in a microplate well for evaluation. As controls (reference samples) a series of blood dilutions in DD water such 20, 30 and 50 µl in 500 µl DD water was prepared. Then, out of each sample, 100 µl is transferred into a microplate well. A good blood sample recovery between 95 and 101% was measured by the UV-VIS Hemoglobin determination at 400 nm.

Sample Concentration by Using a Step-Wise Reconstitution Scheme

A paramagnetic bead mix, reconstitution buffer composition with an internal standard and protocol were developed for the efficient cleanup of serum samples prior to vitamin D analysis. This was first tested and optimized for the performance of protein removal. Below the reagents, materials and protocol are listed below:

| | 1 Tip | 2 Tips | 3 Tips | 1 Tip | 2 Tips | 3 Tips |
|---|---|---|---|---|---|---|
| Dilution 1 | 5 | 2.73 | 1.96 | Tip 1 dry 10 µl Reconstitution buffer 50 µl | Tip 1 dry 10 µl Reconstitution buffer 60 µl Left over sample 50 µl Tip 2 10 µl | Tip 1 dry 10 µl Reconstitution buffer 70 µl Left over sample 60 µl Tip 2 10 µl |

|  | 1 Tip | 2 Tips | 3 Tips | 1 Tip | 2 Tips | 3 Tips |
|---|---|---|---|---|---|---|
|  |  |  |  |  |  | Left over sample 50 μl |
|  |  |  |  |  |  | Tip 2 10 μl |
|  |  |  |  | Transfer 40 μl | Transfer 40 μl | Transfer 40 μl |
| Dilution 2 | 4.75 | 5.25 | 5.88 | Internal Std. 20 μl | Internal Std. 20 μl | Internal Std. 20 μl |
|  |  |  |  | Magnetic Particle Mix 20 μl | Magnetic Particle Mix 20 μl | Magnetic Particle Mix 25 μl |
|  |  |  |  | OPRVI 110 μl | OPRVI 130 μl | OPRVI 150 μl |
|  |  |  |  | Endvol. 90 μl | Endvol. 210 μl | Endvol. 235 μl |
| Dilution total | 23.75 | 14.32 | 11.53 | Transfer volume, 80 μl | Transfer volume, 80 μl | Transfer volume, 80 μl |

Test sample extraction of tips with spiked whole blood

| MM Protocol - MeOH + ZnSO$_4$ | | |
|---|---|---|
| Sample | 25 μl | 1. Transfer 25 μl calibrator/blood to 2 ml tube |
| Lysis buffer (water) | 60 μl | 2. Add 60 μl lysis buffer and mix by pipetting 3x |
| Internal Standard (in MeOH)* | 20 μl | 3. Add 20 μl internal standard mix |
| Beads (Type I) | 40 μl | 4. Add 40 μl MagSiMUS-TDM$^{PREP}$ Type I beads and mix by pipetting 3X |
| Precipitation reagent (MeOH/ZnSO4)** | 250 μl | 5. Add 260 μl precipitation reagents and mix by pipetting 10x |
| Total | 395 μl | 6. Magnetic separation for 2 minutes on MM 12 + 12 |
|  |  | 7. Transfer 100 μl sample to clean sample vial with insert |

**Precipitation reagent

| # sample | Water | MeOH | ZnSO4 (2M) | % MeOH | % water | ZnSO4 (mM) |
|---|---|---|---|---|---|---|
| 1 | 17.5 | 232.5 | 10 | 89.4% | 10.6% | 76.9 |
| 100 | 1750 | 23250 | 1000 | 89.4% | 10.6% | 76.9 |
| Calculation |  | MeOH |  | 63.9% |  |  |
|  |  | ZnSO4 |  | 48.7 mM |  |  |
|  |  | Dilution |  | 15.8× |  |  |

| 1 Tip | | 2 Tips | |
|---|---|---|---|
| Tip 1 | 10 μl | Tip 1 | 10 μl |
| Reconstitution buffer | 50 μl | Reconstitutional buffer | 60 μl |
|  |  | Left over sample | 50 μl |
|  |  | Tip | 10 μl |
| Transfer | 40 μl | Transfer | 40 μl |
| Internal Std. | 20 μl | Internal Std. | 20 μl |
| Magnetic Particle Mix | 20 μl | Magnetic Particle Mix | 20 μl |
| OPRVI | 120 μl | OPRVI | 120 μl |
| End volume. | 200 μl | End volume. | 200 μl |
| Transfer volume. | 80 μl | Transfer volume. | 80 μl |

| LCMs conditions: | |
|---|---|
| LC: | Nexera X2 UHPLC |
| MS: | LCMS 8050 |
| Column: | Phenomenex Kinetex XB C18, 2.6 μm, 2.1 × 50 mm |
| Guard column: | Guard Ultra Cartidges, UHPLC C18 for 2.1 mm ID columns |
| Mobile phase A: | 2 mM ammonium formate + 0.1% formic acid in water |
| Mobile phase B: | 2 mM ammonium formate + 0.1% formic acid in MeOH |
| Flow: | 0.5 ml/min |
| Pump: | 60% B |
| Gradient: | 60-100% B (2 min) |
| Column oven: | 50 C. |
| Injection volume: | 5 μl |

| Time | Module | Command | Value | Comment |
|---|---|---|---|---|
| 1.50 | Controller | Event | 2 | Column effluent to MS |
| 2.00 | Pumps | Pump B conc. | 100 | |
| 3.00 | Pumps | Pump B conc. | 100 | |
| 3.01 | Pumps | Pump B conc. | 60 | |
| 3.50 | Controller | Event | 2 | Column effluent diverted from MS |
| 3.51 | Controller | Stop | | |

| Source conditions: | |
|---|---|
| Nebulizing gas: | 3 L/min |
| Heating gas: | 10 L/min |
| Interface temp.: | 300 C. |
| Desolvation line: | 250 C. |
| Heat block temp.: | 400 C. |
| Drying gas: | 10 L/min |
| Interface voltage: | 4.5 kV |
| Dwell time: | 34 ms |
| Pause time: | 3 ms |
| Ionisation: | ESI positive |
| Scan type: | MRM |

Transition

| Compound | RT (min) | Precursor | Product (m/z) | Target Dwell Time | Target 01 Pre Bias | Target Collision Energy | Target 03 Pre Bias |
|---|---|---|---|---|---|---|---|
| Tacrolimus | | 821.6 | 768.4 | 34 | -30 | -27 | -24 |
| d2 Tacrolimus | | 825.1 | 772.4 | 34 | -24 | -20 | -40 |
| Sirolimus | | 931.5 | 864.45 | 34 | -26 | -20 | -24 |
| 13Cd3 Sirolimus | | 935.3 | 864.5 | 34 | -26 | -20 | -24 |
| Everolimus | | 975.4 | 908.5 | 34 | -28 | -20 | -26 |
| 13C2d4 Everolimus | | 981.7 | 914.5 | 34 | -28 | -20 | -26 |
| Cyclosporin A | | 1219.9 | 1202.6 | 34 | -28 | -23 | -24 |
| D12 Cyclosporin A | | 1232 | 1214.8 | 34 | -28 | -19 | -20 |

Test Sample Extraction with Spiked Whole Blood

Method

Whole blood was spiked with everolimus and sirolimus and the tips were "loaded" with blood.

Sample of this blood was stored at −20, together with a spiked PBS buffer as reference. The tips were air dried 2 days and stored in a plastic bag in the fridge until analysis.

The whole blood sample and a control sample (Recipe, level III) were prepared according to the standard MagSiMUS-TDM$^{PREP}$ Type 1 protocol.

Blood from tips were extracted by placing the tips on a dull 200 μl pipette tip and incubating the tip in 50 μl water in a well of a PCR plate for 10 seconds and then pipetting up and down 10 times (tip1).

Also, 2 tips were extracted in the same well with 60 μl water (tip 2).

After extraction, 40 μl sample was used for protein removal protocol.

Result

Table 1. Concentration (ng/ml) sirolimus and everolimus in spiked whole blood, control sample (Recipe, level III) and after sampling whole blood with a tip. Extraction performed in duplicate.

| | | Corrected concentration | | | | Corrected ISTD (x2) | |
|---|---|---|---|---|---|---|---|
| Sample | Nr | Sirolimus | Everolimus | Sirolimus | Everolimus | Sirolimus | Everolimus |
| PBS control | 0 | 58.6 | 21.0 | 87.9 | 42.0 | 87.9 | 42.0 |
| Spike WB | 1 | 79.7 | 41.6 | 119.5 | 83.3 | 119.5 | 83.3 |
| Spike WB | 2 | 90.7 | 45.0 | 136.0 | 89.9 | 136.0 | 89.9 |
| Control III | 3 | 13.4 | 9.9 | 20.0 | 19.8 | 20.0 | 19.8 |
| Control III | 4 | 15.4 | 6.8 | 23.1 | 13.7 | 23.1 | 13.7 |
| tip 1 | 5 | 14.1 | 6.2 | 21.1 | 12.5 | 42.2 | 25.0 |
| tip 1 | 6 | 13.8 | 5.8 | 20.7 | 11.6 | 41.4 | 23.2 |
| tip 2 | 7 | 28.2 | 12.2 | 42.3 | 24.3 | 84.5 | 48.7 |
| tip 2 | 8 | 22.4 | 12.0 | 33.7 | 24.0 | 67.3 | 48.1 |

| | | | Recovery | |
|---|---|---|---|---|
| Sample | Sirolimus (ng/ml) | Everolimus (ng/ml) | Sirolimus (%) | Everolimus (%) |
| PBS control | 87.9 | 42.0 | 68.8% | 48.5% |
| Spike WB | 127.8 | 86.6 | 100.0% | 100.00% |
| Control III | 21.6 | 16.8 | | |
| tip 1 | 41.8 | 24.1 | 32.7% | 27.8% |
| tip 2 | 75.9 | 48.4 | 59.4% | 55.9% |

Conclusion

Tips could be used successfully to measure a whole blood sample spiked with everolimus and sirolimus Using 2 tips for extraction doubled the concentration (1.8× for sirolimus and 2.0× for everolimus) compared to 1 tip Recovery of sirolimus is 60% and for everolimus 56% when using 2 tips In some embodiments, the present application is directed toward a method to analyze target analyte compounds from a fluid biological sample by using a microfluidic sample device comprising a hollow cartridge and an adsorbent body unit. The method comprises soaking and storing the fluid biological sample in the adsorbent body unit, wherein the adsorbent body unit comprises one or more single layer structures, wherein different functional groups densities of COOH, $NH_2$, OH, $TiO_2$, and/or $ZrO_2$ are present in each of the one or more single layer structures as a binding tool for a pre-cleaning step, wherein a first coating comprising Butylated Hydroxyanisole (BHA), Butylated Hydroxytoluene (BHT), -ethoxyquin, polyvinylpyrrolidone (PVP), polyacrylic acid (PAA), polyethyleneimine (PEI), sorbitan esters, polyethoxy sorbitan esters octylphenoxypolyethoxyethanol, $Na_2$-EDTA, Na-citrate, and/or hydrogels is present on each of the one or more single layer structures as artificial antioxidants and as active hydrophilic compounds, wherein the adsorbent body unit is positioned at a distal end of the hollow cartridge and a proximal end of the hollow cartridge comprises a passage that is configured to be connected to a pipette head of an automated operation device, and wherein the automated operation device is configured to change a position of the pipette head in sequential steps. The fluid biological sample is aspirated into the hollow cartridge through the adsorbent body unit. The fluid biological sample is temporarily stored in the hollow cartridge for up to 600 seconds. The fluid biological sample is released into a first vial or a first well. The fluid biological sample is aspirated back into the hollow cartridge at least one time. A predefined volume of the fluid biological sample is transferred into a second well or a second vial different than the first well and the first vial. Abundant non-analytical compounds of the fluid biological sample are removed by: adding an internal standard, wherein the internal standard comprises D6-25OH-Vitamin D3, D3-Thiamine diphosphate (TDP), D3-Pyridoxal-5'-phosphate (PLP), [13C, $^2H_7$]-apixaban, [$^{13}C_6$]-dabigatran, [$^{13}C_6$]-rivaroxaban, or [$^2H_6$]-edoxaban; adding a first set of coated magnetic beads, wherein the first set of coated magnetic beads comprise silica beads coated with a second coating, wherein the second coating comprises one or more functional groups selected from the group consisting of —OH, —COOH, —$NH_2$, R—$SO_2$—OH, —$NH_2$; —RNH, —$R_2$N, $CH_3$, —$C_2H_5$, —$C_4H_9$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_6H_5$, —$ZrO_2$, $TiO_2$, $C_6H_9NO_6$, phenylhexyl, biphenyl, hydroxyapatite, boronic acid, activated carbon, fullerenes, latex, polyvinyl alcohol, melamine, and chitin; and adding a depletion buffer comprising mixtures of organic solvents and alkaline solutions, wherein the organic solvents or alkaline solutions comprise NaOH, KOH, $NH_4OH$, $(NH_4)_2SO_4$, $(NH_4)CH_3COO$, $ZnSO_4$, $MgSO_4$, $K_4[Fe(CN)_6]$, $CuSO_4$, $AgNO_3$, NaCl, KCl, $MgCl_2$, $(CH_3COO)_2Pb$, $FeCl_3$, $HNO_3$, $HClO_4$, $H_2SO_4$, HCl, $CF_3COOH$, $CCl_3COOH$, $CH_3COOH$, CHOOH, wherein the pH-value is in the range of 0 to 14, and wherein an ionic strength between the depletion buffer and the fluid biological sample is between 1 mM and 5000 mM. The abundant non-analytical compounds of the fluid biological sample are separated by using a magnetic separator. The target analyte compounds of the fluid biological sample are received in the supernatant. Alternatively, at least some of the received target analyte compounds are bound to a second set of coated magnetic beads that are different than the first set of coated magnetic beads and eluting the received target analyte compounds thereafter. The received target analyte compounds are analyzed with one or more readout systems used in combination with one or more specific detectors, wherein the readout systems are selected from the group consisting of immunoassays, GC, HPLC, LC, and CE, and the specific detectors are selected from the group consisting of MS/MS, MS, FID, EDC, UV-VIS-spectrometer, IR-spectrometer, fluorescence, and chemiluminescence immunoassay. In some embodiments, the fluid biological sample is used as a reconstitution buffer composition for at least one other fluid biological sample in order to achieve higher target analyte compounds concentrations in relation to the starting concentration of the target analyte compounds. In further embodiments, the at least one other fluid biological sample is in contact with the reconstitution buffer composition for a period between 1 and 600 seconds, and the reconstitution buffer composition is aspirated into and released from the hollow cartridge by multiple flushing of the reconstitution buffer composition in a multi-directional fashion through the hollow cartridge and adsorbent body unit. In some embodiments, the reconstitution buffer composition comprises sterile bi-distilled water, and sterile aqueous buffers with a pH range between 0 and 14 and with an ionic strength between 1 mM to 5000 mM. In further embodiments, the reconstitution buffer composition comprises salts selected from the group consisting of NaCl, KCl, $MgCl_2$, $Na_3PO_4$, $Na_2HPO_4$, $NaH_2PO_4$, $NaHCO_3$, $KHCO_3$, $(NH_4)CH_3COO$, TRIS salts, Na-dodecyl-sulfate and EDTA disodium salt, and EDTA. In yet further embodiments, the reconstitution buffer composition comprises enzymes selected from the group consisting of proteinase K, trypsin, Lys C, lysosyme, lignin, and organic solvents, wherein the organic solvents are selected from the group consisting of methanol, ethanol, isopropanol, n-propanol, acetonitrile, ethylenglycol, polyethylenglycol, THF, DMSO, and DMFA, and wherein the organic/aqueous ratio range is between 0.01%:99.99% and 99.99%:0.01%. In some embodiments, the adsorbent body unit comprises a hydrophobic, porous adsorbent material having a predefined volume uptake of the fluid biological sample. In some embodiments, the hollow cartridge has a predefined liquid sample volume uptake. In some embodiments, the adsorbent body of the microfluidic device is manufactured from sintered polyethylene and polypropylene material having a pore size ranging from 20 to 100 µm, and wherein the pores are interconnected to each other. In some embodiments, the depletion of the abundant non-analytical compounds comprises using a combination of organic solvents and alkaline, acidic and salts solutions in ratios solvents to alkaline, acidic and salts between 0.1%:100% and 100%:0.1%. In some embodiments, the target analyte compounds are selected from the group consisting of vitamins, antibiotics, steroids, immunosuppressants, drugs, biomarkers of oxidative stress, amino acids and -thiols, RNA/DNA, enzymes, peptides, drugs, metabolites, biomarkers, and nitrogen compounds for protein adulteration.

In some embodiments, the present application is directed toward a hollow cartridge for temporarily storing a fluid biological sample for up to 600 seconds, wherein the storing is performed according to the method to analyze target analyte compounds from a fluid biological sample by using a microfluidic sample device comprising a hollow cartridge and an adsorbent body unit. In some embodiments, the hollow cartridge comprises a membrane. In some embodiments, the hollow cartridge comprises a polymeric adsorbent body unit positioned at the distal end of the hollow cartridge, wherein the proximal end of the hollow cartridge comprises a passage configured to be connected to an automated working station platform. In some embodiments, the hollow cartridge is configured to obtain a reconstituted liquid biological sample from a fluid biological sample, and wherein the hollow cartridge does not comprise a membrane to achieve a separation of the liquid of the adsorbent body unit through the hollow cartridge passage. In some embodiments, the hollow cartridge is configured to obtain a reconstituted liquid biological sample from a fluid biological sample, and wherein the hollow cartridge comprises a membrane to achieve a separation of the liquid of the adsorbent body unit through the hollow cartridge passage, and wherein the membrane is removed by a mechanical force, a pressure, or a vacuum.

In some embodiments, the present application is directed toward a method to analyze target analyte compounds from a dried biological sample by using a microfluidic sample device comprising a hollow cartridge and an adsorbent body unit. The method comprises reconstituting the dried biological sample using a reconstitution buffer composition, wherein the adsorbent body unit comprises one or more single layer structures, wherein different functional groups densities of COOH, $NH_2$, OH, $TiO_2$, and/or $ZrO_2$ are present in each of the one or more single layer structures as a binding tool for a pre-cleaning step, wherein a first coating comprising Butylated Hydroxyanisole (BHA), Butylated Hydroxytoluene (BHT), -ethoxyquin, polyvinylpyrrolidone (PVP), polyacrylic acid (PAA), polyethyleneimine (PEI), sorbitan esters, polyethoxy sorbitan esters octylphenoxypolyethoxyethanol, $Na_2$-EDTA, Na-citrate, and/or hydrogels is present on each of the one or more single layer structures as artificial antioxidants and as active hydrophilic compounds, wherein the adsorbent body unit is positioned at a distal end of the hollow cartridge and a proximal end of the hollow cartridge comprises a passage that is configured to be connected to a pipette head of an automated operation device, wherein the automated operation device is configured to change a position of the pipette head in sequential steps, and wherein the reconstitution buffer composition is dispensed in a first vial or a first well. The reconstituted dried biological sample is soaked and stored in the adsorbent body unit. The reconstituted dried biological sample is aspirated into the hollow cartridge through the adsorbent body unit using a predefined amount of the reconstitution buffer composition. The reconstituted dried biological sample is temporarily stored in the hollow cartridge for up to 600 seconds. The reconstituted dried biological sample is released into the first vial or the first well. The reconstituted dried biological sample is aspirated back into the hollow cartridge at least one time. A predefined volume of the reconstituted dried biological sample is transferred into a second well or a second vial. Abundant non-analytical compounds of the reconstituted dried biological sample are removed by: adding an internal standard, wherein the internal standard comprises D6-25OH-Vitamin D3, D3-Thiamine diphosphate (TDP), D3-Pyridoxal-5'-phosphate (PLP), [$^{13}C$, $^2H_7$]-apixaban, [$^{13}C_6$]-dabigatran, [$^{13}C_6$]-rivaroxaban, or [$^2H_6$]-edoxaban; adding a first set of coated magnetic beads, wherein the first set of coated magnetic beads comprise silica beads coated with a second coating, wherein the second coating comprises one or more functional groups selected from the group consisting of —OH, —COOH, —$NH_2$, R—$SO_2$—OH, —$NH_2$; —RNH, —$R_2N$, $CH_3$, —$C_2H_5$, —$C_4H_9$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_6H_5$, —$ZrO_2$, $TiO_2$, $C_6H_9NO_6$, phenylhexyl, biphenyl, hydroxyapatite, boronic acid, activated carbon, fullerenes, latex, polyvinyl alcohol, melamine, and chitin; and adding a depletion buffer comprising mixtures of organic solvents and alkaline solutions, wherein the organic solvents or alkaline solutions comprise NaOH, KOH, $NH_4OH$, $(NH_4)_2SO_4$, $(NH_4)CH_3COO$, $ZnSO_4$, $MgSO_4$, $K_4[Fe(CN)_6]$, $CuSO_4$, $AgNO_3$, NaCl, KCl, $MgCl_2$, $(CH_3COO)_2Pb$, $FeCl_3$, $HNO_3$, $HClO_4$, $H_2SO_4$, HCl, $CF_3COOH$, $CCl_3COOH$, $CH_3COOH$, CHOOH, wherein the pH-value is in the range of 0 to 14, and wherein an ionic strength between the depletion buffer and the reconstituted dried biological sample is between 1 mM and 5000 mM. The abundant non-analytical compounds of the reconstituted dried biological sample are separated by using a magnetic separator. The target analyte compounds of the reconstituted dried biological sample are received in the supernatant. Alternatively, at least some of the received target analyte compounds are bound to a second set of coated magnetic beads that are different than the first set of coated magnetic beads and eluting the received target analyte compounds thereafter. The received target analyte compounds are analyzed with one or more readout systems used in combination with one or more specific detectors, wherein the readout systems are selected from the group consisting of immunoassays, GC, HPLC, LC, and CE, and the specific detectors are selected from the group consisting of MS/MS, MS, FID, EDC, UV-VIS-spectrometer, IR-spectrometer, fluorescence, and chemiluminescence immunoassay. In some embodiments, the reconstituted dried biological sample is used as a reconstitution buffer composition for at least one other reconstituted dried biological sample in order to achieve higher target analyte compounds concentrations in relation to the starting concentration of the target analyte compounds. In further embodiments, the at least one other reconstituted dried biological sample is in contact with the reconstitution buffer composition for a period between 1 and 600 seconds, and the reconstitution buffer composition is aspirated into and released from the hollow cartridge by multiple flushing of the reconstitution buffer composition in a multi-directional fashion through the hollow cartridge and adsorbent body unit. In some embodiments, the reconstitution buffer composition comprises sterile bi-distilled water, and sterile aqueous buffers with a pH range between 0 and 14 and with an ionic strength between 1 mM to 5000 mM. In further embodiments, the reconstitution buffer composition comprises salts selected from the group consisting of NaCl, KCl, $MgCl_2$, $Na_3PO_4$, $Na_2HPO_4$, $NaH_2PO_4$, $NaHCO_3$, $KHCO_3$, $(NH_4)CH_3COO$, TRIS salts, Na-dodecyl-sulfate and EDTA disodium salt, and EDTA. In yet further embodiments, the reconstitution buffer composition comprises enzymes selected from the group consisting of proteinase K, trypsin, Lys C, lysozyme, lignin, and organic solvents, wherein the organic solvents are selected from the group consisting of methanol, ethanol, isopropanol, n-propanol, acetonitrile, ethylenglycol, polyethylenglycol, THF, DMSO, and DMFA, and wherein the organic/aqueous ratio range is between 0.01%:99.99% and 99.99%:0.01%. In some embodiments, the adsorbent body unit comprises a hydrophobic, porous adsorbent material having a predefined volume uptake of the reconstituted dried biological sample. In some embodiments, the hollow cartridge has a predefined sample volume uptake. In some embodiments, the adsorbent body of the microfluidic device is manufactured from sintered polyethylene and polypropylene material having a pore size ranging from 20 to 100 μm, and wherein the pores are interconnected to each other. In some embodiments, the depletion of the abundant non-analytical compounds comprises using a combination of organic solvents and alkaline, acidic and salts solutions in ratios solvents to alkaline, acidic and salts between 0.1%:100% and 100%:0.1%. In some embodiments, the target analyte compounds are selected from the group consisting of vitamins, antibiotics, steroids, immunosuppressants, drugs, biomarkers of oxidative stress, amino acids and -thiols, RNA/DNA, enzymes, peptides, drugs, metabolites, biomarkers, and nitrogen compounds for protein adulteration.

In some embodiments, the present application is directed toward a hollow cartridge for temporarily storing a reconstituted dried biological sample for up to 600 seconds, wherein the storing is performed according to the method to analyze target analyte compounds from a dried biological sample by using a microfluidic sample device comprising a hollow cartridge and an adsorbent body unit. In some embodiments, the hollow cartridge comprises a membrane. In some embodiments, the hollow cartridge comprises a polymeric adsorbent body unit positioned at the distal end of the hollow cartridge, wherein the proximal end of the hollow cartridge comprises a passage configured to be connected to an automated working station platform. In some embodiments, the hollow cartridge is configured to obtain a reconstituted liquid biological sample from a dried biological sample, and wherein the hollow cartridge does not comprise a membrane to achieve a separation of the liquid of the adsorbent body unit through the hollow cartridge passage. In some embodiments, the hollow cartridge is configured to obtain a reconstituted liquid biological sample from a dried biological sample, and wherein the hollow cartridge comprises a membrane to achieve a separation of the liquid of the adsorbent body unit through the hollow cartridge passage, and wherein the membrane is removed by a mechanical force, a pressure, or a vacuum.

The invention claimed is:

1. A microfluidic sample device configured to analyze target analyte compounds from a fluid biological sample, the microfluidic sample device comprising:
    a hollow cartridge and an absorbent body unit, wherein:
        the absorbent body unit comprises a filter paper, a capillary pipette tip, or a modified polymeric sintered filter body that is configured to be attached to the hollow cartridge with a pipette-like geometry to soak and store the fluid biological sample into the absorbent body unit;
        the absorbent body unit comprises one or more single layer structures;
        different functional groups densities of COOH, $NH_2$, OH, $TiO_2$, and/or $ZrO_2$ are present in each of the one or more single layer structures as a binding tool for a pre-cleaning step;
        a first coating comprising Butylated Hydroxyanisole (BHA), Butylated Hydroxytoluene (BHT), -ethoxyquin, polyvinylpyrrolidone (PVP), polyacrylic acid (PAA), polyethyleneimine (PEI), sorbitan esters, polyethoxy sorbitan esters octylphenoxypolyethoxyethanol, $Na_2$-EDTA, Na-citrate and/or hydrogels is present on each of the one or more single layer structures as artificial antioxidants and as active hydrophilic compounds;
        the absorbent body unit is positioned at a distal end of the hollow cartridge and a proximal end of the hollow cartridge comprises a passage that is configured to be connected to a pipette head of an automated operation device; and
        the hollow cartridge comprises a membrane to achieve a separation of the liquid of the absorbent body unit through the hollow cartridge passage.

2. The microfluidic sample device of claim 1, wherein the automated operation device is an automated working station platform.

3. The microfluidic sample device of claim 1, wherein the hollow cartridge is configured to obtain a reconstituted liquid biological sample from the fluid biological sample, and wherein the membrane is configured to be removed by a mechanical force, a pressure, or a vacuum.

4. The microfluidic sample device of claim 1, wherein the absorbent body unit is based on a hydrophobic, porous absorbent material having a predefined volume uptake of the fluid biological sample.

5. The microfluidic sample device of claim 1, wherein the hollow cartridge has a predefined liquid sample volume uptake.

6. The microfluidic sample device of claim 1, wherein the absorbent body unit of the microfluidic sample device is manufactured from sintered polyethylene and polypropylene material having a pore size ranging from 20 to 100 μm, and wherein the pores are interconnected to each other.

7. The microfluidic sample device of claim 1, wherein the storing of the fluid biological sample comprises storing the fluid biological sample for up to 600 s.

8. A microfluidic sample device configured to obtain a reconstituted liquid biological sample from a dried biological sample, the microfluidic sample device comprising:
    a hollow cartridge and an absorbent body unit, wherein:
        the absorbent body unit comprises a filter paper, a capillary pipette tip, or a modified polymeric sintered filter body that is configured to be attached to the hollow cartridge with a pipette-like geometry;
        the absorbent body unit comprises one or more single layer structures;
        different functional groups densities of COOH, $NH_2$, OH, $TiO_2$, and/or $ZrO_2$ are present in each of the one or more single layer structures as a binding tool for a pre-cleaning step;
        a first coating comprising Butylated Hydroxyanisole (BHA), Butylated Hydroxytoluene (BHT), -ethoxyquin, polyvinylpyrrolidone (PVP), polyacrylic acid (PAA), polyethyleneimine (PEI), sorbitan esters, polyethoxy sorbitan esters octylphenoxypolyethoxyethanol, $Na_2$-EDTA, Na-citrate and/or hydrogels is present on each of the one or more single layer structures as artificial antioxidants and as active hydrophilic compounds;
        the absorbent body unit is positioned at a distal end of the hollow cartridge and a proximal end of the hollow cartridge comprises a passage that is configured to be connected to a pipette head of an automated operation device; and
        the hollow cartridge comprises a membrane to achieve a separation of the liquid of the absorbent body unit through the hollow cartridge passage; and
        the membrane is configured to be removed by a mechanical force, a pressure, or a vacuum.

* * * * *